(12) United States Patent
Appakalai et al.

(10) Patent No.: US 11,464,808 B2
(45) Date of Patent: Oct. 11, 2022

(54) TISSUE CONSTRUCTS INCLUDING PANCREAS DERIVED MICROVESSEL FRAGMENTS AND RELATED METHODS

(71) Applicant: University of Louisville Research Foundation, Inc., Louisville, KY (US)

(72) Inventors: Balamurugan Appakalai, Louisville, KY (US); Stuart K. Williams, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 338 days.

(21) Appl. No.: 16/609,063

(22) PCT Filed: Apr. 27, 2018

(86) PCT No.: PCT/US2018/029815
§ 371 (c)(1),
(2) Date: Oct. 28, 2019

(87) PCT Pub. No.: WO2018/200968
PCT Pub. Date: Nov. 1, 2018

(65) Prior Publication Data
US 2020/0054685 A1 Feb. 20, 2020

Related U.S. Application Data

(60) Provisional application No. 62/491,895, filed on Apr. 28, 2017.

(51) Int. Cl.
*A61K 35/44* (2015.01)
*A61K 35/39* (2015.01)
*C12N 5/071* (2010.01)

(52) U.S. Cl.
CPC ............ *A61K 35/44* (2013.01); *A61K 35/39* (2013.01); *C12N 5/0677* (2013.01); *C12N 2513/00* (2013.01); *C12N 2533/54* (2013.01)

(58) Field of Classification Search
None
See application file for complete search history.

(56) References Cited

U.S. PATENT DOCUMENTS

2002/0142459 A1* 10/2002 Williams ............. C12N 5/0691
435/366
2010/0196433 A1 8/2010 Williams et al.
2012/0065048 A1 3/2012 Chapman, Jr. et al.
2015/0231182 A1 8/2015 Boyd et al.

FOREIGN PATENT DOCUMENTS

WO 2006130851 A2 12/2006
WO 2007009036 A2 1/2007

OTHER PUBLICATIONS

Henderson et al, Quarterly J Experimental Physiology, 1985, 70: 357-356. (Year: 1985).*
Hoying et al, In Vitro Cellular Developmental Biology—Animal, 1996, 32(7):409-419. (Year: 1996).*
Hiscox et al, Tissue Engineering: Pt A, 2008, 14(3):433-440. (Year: 2008).*
Definition for "Isolate", Merriam-Webster Online dictionary, accessed Mar. 25, 2022. (Year: 2022).*
Laschke et al, Trends in Biotechnology, Aug. 2015, 33(8):442-448. (Year: 2015).*
Laschke et al, Biotechnology Advances, 2016, 34:112-121 (epub Dec. 2015). (Year: 2016).*
Nunes et al, Microcirculation, 2011, 17(7):557-567 (Author manuscript provided). (Year: 2011).*
Favaro et al.; "Primary and immortalised human pancreatic islet endothelial cells: phenotypic and immunological characterisation"; Diabetologia, Nov. 15, 2005, vol. 48, No. 12, pp. 2552-2562.

* cited by examiner

*Primary Examiner* — Allison M Fox
(74) *Attorney, Agent, or Firm* — WCF IP

(57) ABSTRACT

A tissue construct is provided that comprises a pancreas derived microvessel fragment and a pancreatic islet cell. The pancreas derived microvessel fragment and the pancreatic islet cell can be incorporated into a biocompatible medium. Tissue constructs can be comprised of other cells, such as stem cells, combined with the pancreas derived microvascular fragment. Methods for isolating microvessel fragments from a pancreas are also provided and include enzymatic digestion of pancreatic tissue and separation of microvessel fragments from endocrine and exocrine tissue. Methods for treating diabetes are further provided and include administration of the tissue constructs.

19 Claims, 24 Drawing Sheets

TISSUE CONSTRUCTS INCLUDING PANCREAS DERIVED MICROVESSEL FRAGMENTS AND RELATED METHODS

RELATED APPLICATIONS

This application claims priority from U.S. Provisional Application Ser. No. 62/491,895, filed Apr. 28, 2017, the entire disclosure of which is incorporated herein by this reference.

TECHNICAL FIELD

The presently-disclosed subject matter relates to tissue constructs including pancreas derived microvessel fragments and related methods. In particular, certain embodiments of the presently-disclosed subject matter relate to tissue constructs including pancreas derived microvessel fragments, methods of isolating the pancreas derived microvessel fragments, and the use of such tissue constructs for the treatment of diabetes.

BACKGROUND

Islet cell transplantation is an effective beta-cell replacement therapy, which remains the most promising technology for the treatment of type 1 diabetes. The long-term clinical outcomes of islet transplantation in selected centers are now comparable to the outcomes of whole-pancreas transplantation, with 50-70% of patients achieving insulin independence at 5 years. However, existing human islet isolation techniques completely severs the islet vasculature. Unlike whole pancreas transplantation, rapid and adequate revascularization is important for the survival and function of transplanted islets. This usually depends on reestablishment of new vessels within islet grafts to derive blood flow from the host vascular system. An estimated <50% of infused islets become stably engrafted, despite administration of a large quantity of islets in the perfusate infused to the recipient. Islet grafts have significantly less vascular supply and lower oxygen tension than normal islets. This results in limited inosculation with the host circulation, and many islets die due to poor revascularization. Prevascularizing islets prior to transplantation can potentially improve islet survivability and function by aiding islet-to-host inosculation. Rapid and adequate islet revascularization is important for the immediate survival and long-term function of transplanted islets.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

The presently-disclosed subject matter includes tissue constructs including pancreas derived microvessel fragments and related methods. In particular, the presently-disclosed subject matter includes tissue constructs including pancreas derived microvessel fragments, methods of isolating the pancreas derived microvessel fragments, and the use of such tissue constructs for the treatment of diabetes.

In some embodiments, a tissue construct is provided that comprises a pancreas derived microvessel fragment and a pancreatic islet cell. In some embodiments, the tissue construct further comprises a biocompatible medium such that, in certain embodiments, the pancreas derived microvessel fragment and the pancreatic islet cell are incorporated into the biocompatible medium. In some embodiments, the biocompatible medium comprises a hydrogel, such as, in certain embodiments, a hydrogel comprised of a material selected from the group consisting of agarose, alginate, collagen, fibrinogen, fibrin, laminin, a polyoxyethylene-polyoxypropylene block copolymer, silicone, polysaccharide, polyethylene glycol, and polyurethane. In some embodiments, the hydrogel is comprised of collagen type I.

In some embodiments, a tissue construct is provided that comprises a pancreas derived microvessel fragment in combination with one or more other cells and/or one or more stem cells either alone and/or in combination with a pancreatic islet cell. In some embodiments, the cells for the tissue construct are obtained from a human subject such as a human subject in need of treatment.

Further provided, in some embodiments, are methods for isolating microvessel fragments from a pancreas that comprise the steps of subjecting an amount of pancreatic tissue to an enzymatic digestion to produce a slurry of digested pancreatic tissue; centrifuging the slurry of digested tissue in a first centrifuge tube at a low speed sufficient to deposit endocrine and exocrine tissue at the bottom of the centrifuge tube; collecting the supernatant from the first centrifuge tube in a second centrifuge tube; and centrifuging the supernatant at a higher speed sufficient to pellet an amount of microvessel fragments from the pancreatic tissue. In some embodiments of the isolation methods, the methods further include a step of isolating an amount of pancreatic islet cells from the pancreatic tissue.

Still further provided, in some embodiments, are methods for treating diabetes. In some embodiments, a method for treating diabetes is provided that comprises administering to a subject in need thereof an effective amount of a tissue construct comprising a pancreas derived microvessel fragment and a pancreatic islet cell. In some embodiments, administering the tissue construct comprises subcutaneously administering the tissue construct, such as, in certain embodiments, subcutaneously administering the tissue construct at multiple sites in a body of a subject.

Further features and advantages of the presently-disclosed subject matter will become evident to those of ordinary skill in the art after a study of the description, figures, and non-limiting examples in this document.

BRIEF DESCRIPTION OF THE DRAWINGS

(FIG. 1A) human islet and PD-MVFs during islet isolation; (FIG. 1B) CD 31 staining showing numerous PD-MVFs with islets; (FIG. 1C) a higher magnification view of the image shown in FIG. 1B showing PD-MVFs and an islet; (FIG. 1D) UEA-1 staining (green) of PD-MVFs and an islet (red); (FIG. 1E) a high magnification view showing an endothelial lining in PD-MVFs (arrow); and (FIG. 1F) a scanning electron microscopic image of a single PD-MVF.

(FIG. 3A) live cells gated from forward scatter vs. side scatter dot plot; (FIG. 3B) CD45−, CD90+ events gated for identifying (FIG. 3C) CD31 expression where the numbers indicate the percentage of parental gate as shown and where CD31+ cells were 0.24% of the initial cell population (indicated as live gate in FIG. 3A); and (FIG. 3D) graphs showing that numerous endothelial cells (ECs) were present in PD-MVF samples, where the ECs in PD-MVF samples were quantified by FACS analysis of PD-MVF samples collected after pancreas digestion filtered through 100 μm mesh and stained for flow cytometric CD31 expression using LSRII cytometer, and where live cells were gated on a side scatter vs. CD31 PE dot plot to evaluate the percentage of ECs in human (panel A and panel B) and rat (panel C and panel D) PD-MVFs.

(FIG. 4A) sprout initiation (arrows) observed at day 2; (FIG. 4B) endothelial tip and stalk cell formation observed at day 7; and (FIG. 4C) UEA-1 stain confirming the presence of ECs, which formed the building blocks of PD-MVF network formation.

FIGS. 6A-6B include graphs showing gene expression studies from islet isolation samples (PD-MVFs) identify relative mRNA expression levels of: (FIG. 6A) known genes associated with the Notch signaling pathway where the cDNA synthesis and quantitative real-time PCR were performed on four biological independent samples, and all expression levels were normalized to β-actin; and (FIG. 6B) notch signaling pathway end target gene expression of HES1 and HEY1 performed for 3 groups of freshly collected human PD-MVFs, where relative mRNA levels of HES1, and HEY1 were found to be significantly higher in the PD-MVF cultured group, and where that upregulation of Notch target genes indicated increased activity of the Notch pathway in the culture group, further indicating the role of the Notch Pathway during PD-MVF EC sprouting.

(FIG. 7C) CD31 stain demonstrating the presence of intra-islet ECs in fresh islets (arrow); (FIG. 7D) islets when co-cultured with PD-MVFs in a collagen gel form PIVs at day 14; (FIG. 7E) a magnified image (60×) of PIV formation in islets; (FIG. 7F) UEA-1 staining confirming that the PIV formation and sprouting is endothelial in origin; and (FIG. 7G-7I) SEM images showing ultrastructure of PIV's.

(FIG. 7J) PD-MVFs when cultured with GFP-islets stimulate intra-islet ECs to form PIVs; (FIG. 7K) a higher magnification of an intra-islet vessel sprout; (FIG. 7L) Tie2 mice islets showing presence of green intra-islet ECs; (FIG. 7M) Tie2 mice intra-islet ECs stimulated to form PIVs in presence of PD-MVFs.

(FIG. 10A) microvessels around rodent islets (arrow) forming intense microvascular structures termed 'vascular baskets'; (FIG. 10B) islets shown within these baskets at 10× magnification; and (FIG. 10C) 20× magnification of an islet showing intra-islet vasculature inosculating with the co-seeded MVFs when cultured in vitro.

(FIG. 11A) an image showing a transplanted gel in nude mouse after implantation; (FIG. 11B) an image showing transplanted graft as observed at day 30; (FIG. 11C) an image showing histological analysis demonstrating the presence of viable islets with vascular network; (FIGS. 11D-11E) images showing the inosculation of fat-derived transplanted vessels with the host (Green-UEA-1 stain and red (dextran infusion); (FIG. 11F) images showing that, in control islets, lesser vascular network was observed when compared to FIG. 11D-11E; and (FIG. 11G) a graph showing quick reversal of diabetes after implanting islets and PD-MVF as a prevascularized construct (blue-sprouted islets or bioengineered islets; control—red).

DESCRIPTION OF EXEMPLARY EMBODIMENTS

Figure 1A:
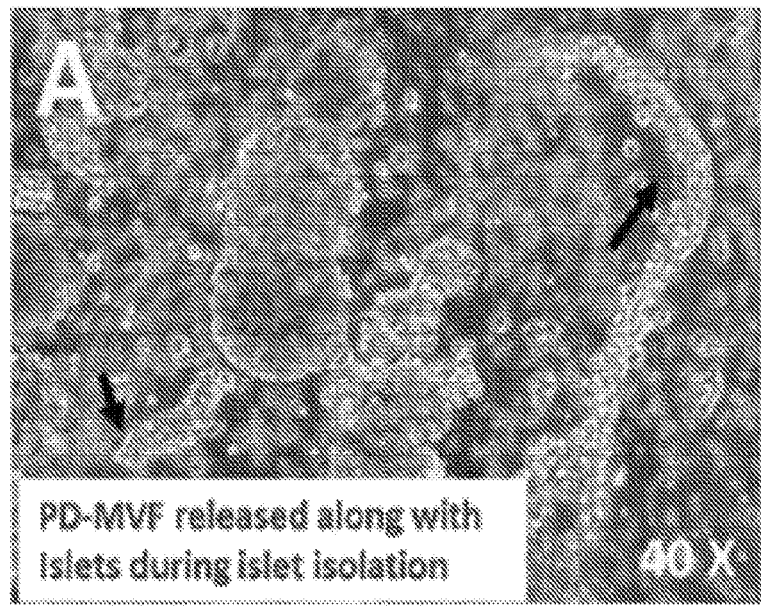
FIGS. 1A-1F includes images showing a morphological assessment of pancreas-derived micro-vessel fragments (PD-MVFs), including images showing.
Figure 1B:
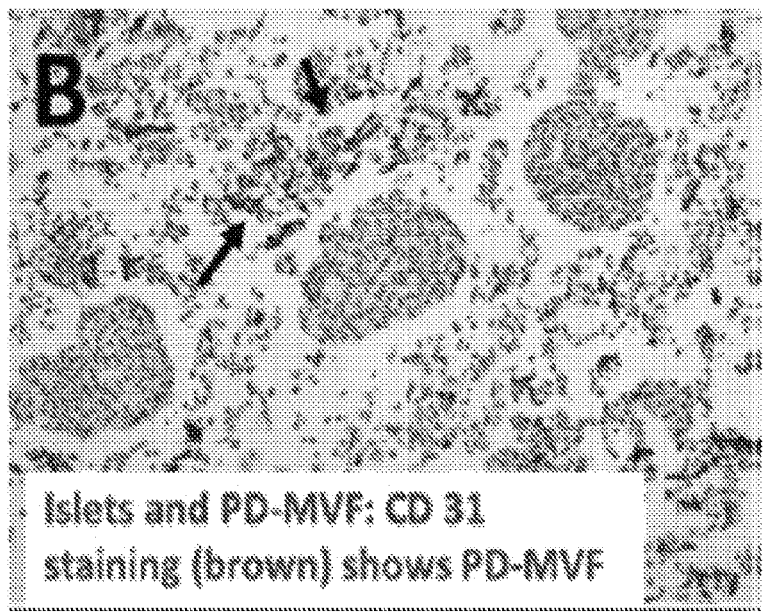
Figure 1C:
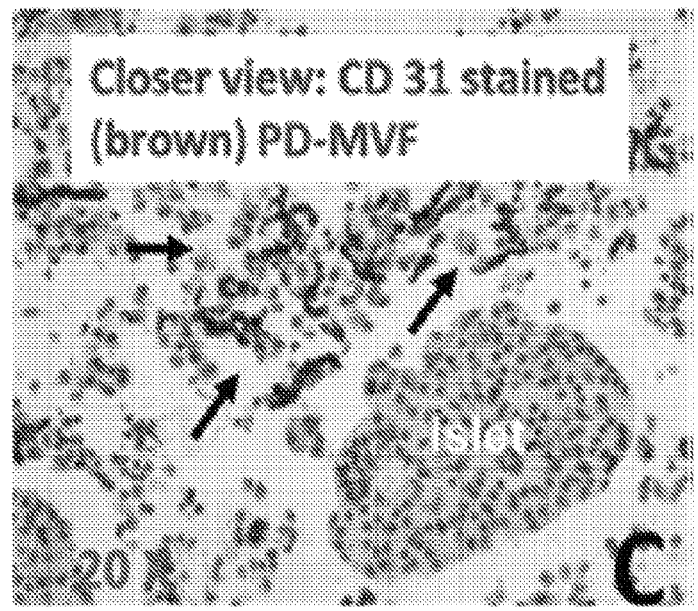
Figure 1D:
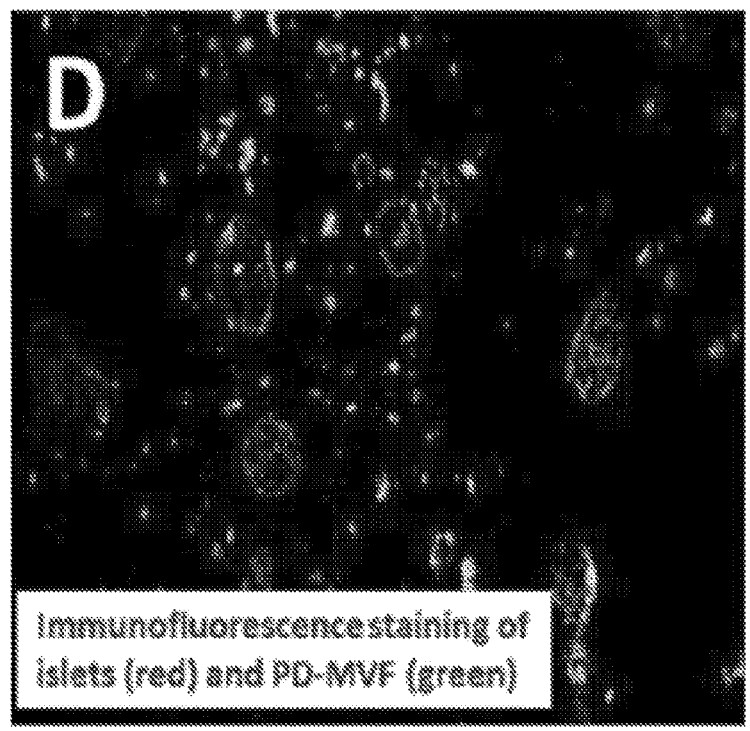
Figure 1E:
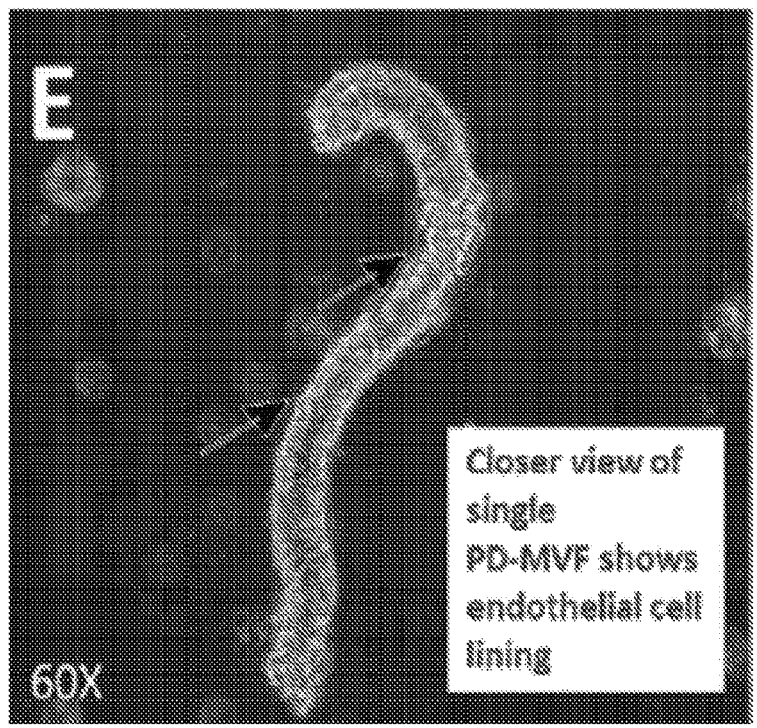
Figure 1F:
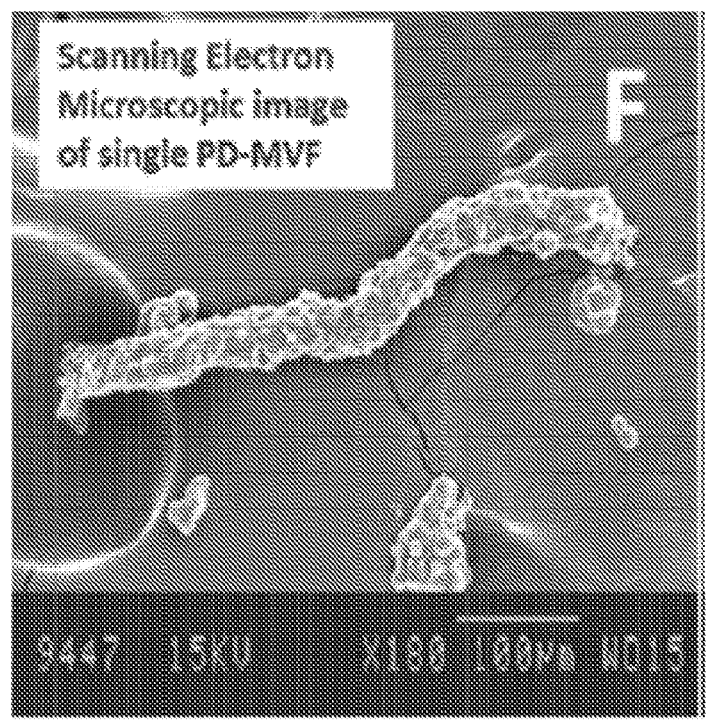

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended), "consist of" (closed), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

Microvessel or microvascular fragments can be isolated from adipose tissue. Those microvessel fragments can be used to create new blood vessels in tissue implants and help in the formation of what has been described as prevascularized tissue constructs. Moreover, islets from pancreatic tissue have also been isolated for the purpose of transplanting the islets. During the process of that islet isolation, the pancreas is subjected to an enzyme-based tissue dissociation that results in the release of islets from surrounding exocrine tissue. Following enzyme digestion, the slurry of digested tissue is subjected to a low speed centrifugation resulting in the deposition of endocrine and exocrine tissue at the bottom of the centrifuge tube. The supernatant is then typically discarded as part of that digestion process. Upon evaluation of the supernatant resulting from that centrifugation process, however, it has now been surprisingly discovered that the supernatant is enriched in microvascular endothelial cell fragments, which are referred to herein as pancreas-derived microvessel fragments or PD-MVFs. As described in detail below, these fragments have been characterized using immunocytochemistry and cytochemistry, and it has been observed that the fragments contain both endothelium and surrounding smooth muscle cells and pericytes, and that the fragments can be utilized in tissue construct for implantation or other administration to a subject.

The presently-disclosed subject matter thus includes tissue constructs including pancreas derived microvessel fragments and related methods. In particular, the presently-disclosed subject matter includes tissue constructs including pancreas derived microvessel fragments, methods of isolating the pancreas derived microvessel fragments, and the use of such tissue constructs for the treatment of diabetes.

In some embodiments, a tissue construct is provided that comprises a pancreas derived microvessel fragment and a pancreatic islet cell. In some embodiments, the tissue construct further comprises a biocompatible medium such that, in certain embodiments, the pancreas derived microvessel fragment and the pancreatic islet cell are incorporated into the biocompatible medium.

The term "tissue construct" or "prevascularized tissue construct" or "engineered tissue construct" are used interchangeably herein to refer to a composition comprising at least one vascular fragment, such as a pancreas derived microvessel fragment, and one or more cells, such as pancreatic islet cells described herein below. The term "vascular fragment" or "vessel fragment" is used herein to refer to a segment or piece of vascular tissue, including at least a part or segment of at least an artery, arteriole, capillary, venule, vein, or a combination thereof. As such, the terms vascular fragment or vessel fragment are further inclusive of the terms "microvessel fragment" or "microvascular fragment," which are used interchangeably herein to refer to a segment or piece of a smaller caliber vascular tissue, such as arterioles, capillaries, and venules. Typically, and as would be recognized by those skilled in the art, a vessel or microvessel includes endothelial cells arranged in a tube surrounded by one or more layers of mural cells, such as smooth muscle cells or pericytes, and can further comprise extracellular matrix components, such as basement membrane proteins.

In some embodiments of the presently-disclosed subject matter, such microvessel fragments from a pancreas can be isolated by obtaining an amount of pancreatic tissue and subsequently subjecting that amount of pancreatic tissue to an enzymatic digestion to produce a slurry of digested tissue. The slurry can then be centrifuged in a first centrifuge tube at a low speed (e.g., 100 G to 200 G) that is sufficient to deposit endocrine and exocrine tissue at the bottom of the first centrifuge tube. The supernatant from the first centrifuge tube can then be collected and placed in a second centrifuge tube, and that second centrifuge tube can be centrifuged at a higher speed (e.g., 2000 G) sufficient to pellet an amount of microvessel fragments. The pelleted microvascular fragments can then be aspirated from a centrifuge tube and readily used in a tissue construct as described herein.

In some embodiments, the tissue constructs that are produced and utilized in conjunction with the presently-disclosed subject matter include the pancreas-derived microvessel fragments incorporated into a suitable biocompatible medium. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGEL™ (BD Biosciences, San Jose, Calif.), polyethylene glycol, dextrans including chemically-crosslinkable or photo-crosslinkable dextrans, and the like, as well as electrospun biological, synthetic, or biological-synthetic blends. In some implementations, the biocompatible medium is comprised of materials that support endothelialization, see, e.g., U.S. Pat. Nos. 5,744,515 and 7,220,276, both of which are incorporated herein by reference. In some implementations, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application (e.g., a particular construct) based on the intended use of the construct, taking into account any parameters that are to be used as well as the effect the selected hydrogel will have on the behavior and activity of the biological materials (e.g., cells). Exemplary hydrogels of the presently-disclosed subject matter can be comprised of polymeric materials including, but not limited to: alginate, collagen (including collagen types I and VI), fibrinogen, elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing. For additional information regarding the materials from which a hydrogel of the presently-disclosed subject matter can be comprised, see, e.g., U.S. Pat. Nos. 7,919,11, 6,991,652 and 6,969,480, each of which are incorporated herein by this reference.

In some embodiments of the presently-disclosed subject matter, as noted above, the tissue constructs are comprised of a pancreas derived microvessel fragment and a pancreatic islet cell. In other embodiments of the presently-disclosed subject matter, a tissue construct can alternatively be provided that include one or more Relevant Cells, as defined herein below, and/or one or more stem cells in combination with the pancreas derived microvessel fragments of the presently-disclosed subject matter.

With respect to the stem cells that can be utilized in accordance with the constructs and methods of the present invention, as used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu. Rev. Cell. Dev. Biol. 17:387-403; Pittinger et al., Science, 284:143-47, 1999; Animal Cell Culture, Masters, ed., Oxford University Press, 2000; Jackson et al., PNAS 96(25):14482-86, 1999; Zuk et al., Tissue Engineering, 7:211-228, 2001; and U.S. Pat. Nos. 5,559,022, 5,672, 346 and 5,827,735. Descriptions of stromal cells, including methods for isolating them, may be found in, among other places, Prockop, Science, 276:71-74, 1997; Theise et al., Hepatology, 31:235-40, 2000; Current Protocols in Cell Biology, Bonifacino et al., eds., John Wiley & Sons, 2000; and U.S. Pat. No. 4,963,489. One of ordinary skill in the art will understand that the stem cells that are selected for inclusion in a tissue construct are typically selected when such cells are appropriate for the intended use of a particular construct.

With respect to the Relevant Cells that can be utilized in accordance with the methods of the present invention, the term "Relevant Cells," as used herein refers to cells that are appropriate for incorporation into a construct of the presently-disclosed subject matter, based on the intended use of that construct. In some embodiments, the term "Relevant Cells" can be used interchangeably with the term "regenerative cells" as the relevant cells described herein have the ability to form a functional tissue following implantation. For example, Relevant Cells that are appropriate for the repair, restructuring, or repopulation of particular damaged tissue or organ will typically include cells or groups of cells that are commonly found in that tissue or organ. In that regard, exemplary Relevant Cells that can be incorporated into the constructs of the presently-disclosed subject matter include neurons, cardiomyocytes, myocytes, vascular and/or gastrointestinal smooth muscle cells, chondrocytes, pancreatic acinar cells, islets of Langerhans, islet beta cells, osteocytes, hepatocytes, Kupffer cells, fibroblasts, myoblasts, satellite cells, endothelial cells, adipocytes, preadipocytes, biliary epithelial cells, and the like. These types of cells may be isolated and used immediately or subjected to culture by conventional techniques known in the art. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022. In some embodiments, and as indicated above, the Relevant Cells comprise pancreatic islet cells, which can be inclusive of pancreatic beta cells, the entire intact islet, and the like.

Further provided, in some embodiments of the presently-disclosed subject matter, are methods of treating diabetes. In some embodiments, a method of treating diabetes is provided that comprises administering to a subject in need thereof an effective amount of a tissue construct comprising a pancreas derived microvessel fragment and a pancreatic islet cell. As used herein, the terms "treatment" or "treating" relate to any treatment of diabetes, including, but are not limited to: reducing the development of diabetes; inhibiting the progression of diabetes; arresting or preventing the further development of a diabetes; reducing the severity of diabetes; ameliorating or relieving symptoms associated with diabetes; and causing a regression of diabetes or one or more of the symptoms associated with diabetes.

Suitable methods for administering a therapeutic tissue construct in accordance with the methods of the presently-disclosed subject matter include, but are not limited to, parenteral administration (including intravascular, intramuscular, and/or intra-arterial administration), subcutaneous administration, intraperitoneal administration, surgical implantation, and local injection. In some embodiments, the tissue constructs of the presently-disclosed subject matter are implanted in a subject, such as by, in some embodiments, subcutaneous administration. In some embodiments, subcutaneously administering the tissue constructs comprises subcutaneously administering one or more tissue constructs at multiple sites in the body of a subject.

Regardless of the particular route of administration, the tissue constructs of the presently-disclosed subject matter are typically administered in amount effective to achieve the desired response. As such, the term "effective amount" is used herein to refer to an amount of the tissue constructs sufficient to produce a measurable biological response (e.g., an increase in the production of insulin). Actual amounts of therapeutic cells in a tissue construct of the presently-disclosed subject matter or the number of tissue constructs used for a particular treatment can be varied so as to administer an amount of the active therapeutic cells(s) (e.g., the pancreatic islet cells) that is effective to achieve the desired therapeutic response for a particular subject and/or application. Of course, the effective amount in any particular case will depend upon a variety of factors including the activity of the therapeutic cells, formulation, the route of administration, combination with other treatments, severity of the condition being treated, and the physical condition and prior medical history of the subject being treated. Preferably, a minimal amount is administered, and the amount is escalated in the absence of dose-limiting toxicity to a minimally effective amount. Determination and adjustment of a therapeutically effective amount, as well as evaluation of when and how to make such adjustments for a particular subject, are known to those of ordinary skill in the art.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

Still further provided, in some embodiments of the presently-disclosed subject matter, are kits that comprise a Relevant Cell (e.g., a pancreatic islet cell) and a pancreas derived microvessel fragment. In some embodiments, the kit can be provided with a first vessel including the Relevant Cell and a second vessel including the pancreas derived microvessel fragment. In other embodiments of the kits, the Relevant Cells and the pancreas derived microvessel fragment are combined and incorporated into a biocompatible medium, such that the kit provides an assembled tissue construct that can readily be administered to a subject. In some embodiments, the kit can further include the materials for producing a biocompatible medium. In some embodiments, a kit comprising a tissue construct or components of a tissue construct of the presently-disclosed subject matter is provided along with instructions for combining the components to produce a tissue construct and/or with instructions for using the tissue construct in a subject.

In some embodiments of the presently-disclosed subject matter, the uses of the microvascular fragments described herein include the treatment of the isolated islet with the microvessel fragments or cells to improve revascularization and inosculation as well as the formation of prevascularized constructs. In some embodiments, the presently-disclosed subject matter further provides for the treatment of islets with the microvascular fragments to improve revascularization and tissue integration of the islets, as well as the creation of prevascularized islet implants for delivery to subcutaneous or intra-muscular sites. In some embodiments, the microvascular fragments described herein can be isolated from a supernatant and used immediately, so as to provide a cell source capable of being used without the need for further regulatory approval. In some embodiments, there is no further manipulation of the microvessel fragments described herein.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-3

Pancreas-derived Microvessel Fragments (PD-MVF) collection. PD-MVF collection was performed after the pancreatic digestion step and during the collection phase of the human islet isolation procedure. Pancreatic digestion was performed using tissue dissociation enzymes and digestion stopped when free islets were observed in the digestion solution. Once the use of digestion in the closed circuit was over (switch time usually between 15-20 min once the digestion was started), fresh RPMI at room temperature was added to the intake container as needed. The digest was collected into 1 L Erlenmeyer flasks prefilled with RPMI and serum, under cold conditions (ice in ice-buckets kept ready to place the flasks in). Four such flasks were previously prepared and kept in the fridge until ready for use. When the 1 L volume reached, the solution was immediately decanted into 250 mL conical tubes for centrifugation at 170 G at 4° C. for 3 minutes. The heavier islets and the acinar fraction settled at the bottom and were collected separately, and the supernatant (PD-MVF rich) was collected in a 1 L flask kept on ice. Multiple flasks were required to collect all the supernatant (4-5 L total volume). Once all the digested tissue was collected (steps 3-5), the supernatant solution was transferred again into 250 mL conical tubes and spun at 170 G for 3 minutes. This separated the fat layer at the top and a smaller acinar fraction as the pellet. That step was repeated once more to separate out as much fat and acinar cells. The PD-MVF enriched supernatant was then spun at high speed 2000 G for 3 minutes to collect the pool of MVF cells. The cells were subsequently aspirated and put in RPMI media containing sera and subjected for further analyses.

Viability assessment. The viability of the micro vessel fragments was assessed using the New Brunswick's NucleoCounter, an automated cell counting device for cell cultures as per the manufacturer's instructions (using the disposable cartridges called NucleoCassettes™, which contain the fluorescent dye PI for staining cell nuclei).

FACS analysis. For FACS analysis, $1 \times 10^6$ PD-MVF cells were washed twice with staining buffer (HBSS+2% FBS+0.02% NaN3) and spun at 500 g for 4 minutes. 50 µL of FcR block (20% concentration) was then added and incubated on ice for 5 minutes. Filtration was performed to remove clumpy cells and 1 mL of plain HBSS was added and spun at 500 g for 4 minutes. Labeling with antibody was then performed for 20-30 minutes on ice with manufacturer recommended concentrations of human monoclonal fluorescent antibodies or the isotype controls (both either from BD or AbCam). Cells were then washed twice with PBS, paraformaldehyde fixed and analyzed on a FACS-calibur instrument.

Collagen gel culture (for in vivo studies). Freshly collected human PD-MVFs and islets (islet:PD-MVFs::1:1000) were cultured in collagen gel (type 1 collagen [Invitrogen, Carlsbad, Calif.]). To prepare the collagen gels (total volume=5 mL), 1.25 mL (4.7 mg/ml 4×DMEM) and L-glutamine was added to 1.945 mL of sterile water to which 1.805 mL collagen was added (final concentration of 3 mg/mL). To form the gel constructs, 0.25 ml of the islet-collagen mixture or islet-collagen-PD-MVF mixture was plated/well in a non-coated 48-well tissue culture plate and allowed to polymerize (37° C., about half an hour). Once polymerized, the set gel was topped with 1 mL of DMEM culture media (Corning Life Sciences, Corning, N.Y.) supplemented with endothelial cell growth supplement (ECGS) and utilized the following day for in vivo nude mice transplantation studies (to check for diabetes reversal).

Nude mice transplantation. Transplantation of collagen gels containing human islets and PD-MVFs in the diabetic (streptozotocin-induced) nude mice were introduced into the subcutaneous space. Isolated human islets and PD-MVFs (1:1000) were embedded in collagen gels (3 mg/ml) along with control groups. Experimental group (n=20; islets and PD-MVFs, $103:1 \times 10^6$ respectively/ml of collagen gel) and controls (islets alone ($10^3$); PD-MVFs alone ($1 \times 10^6$)) were used. These gel constructs were implanted subcutaneously and the mice monitored for diabetes reversal as previously published (Loganathan et al., 2018).

Example 1—Isolation and Characterization of Pancreas-Derived Microvessel Fragments (PD-MVF) for Improving Human Islet Function.

Previously, researchers have utilized microvessel fragments (MVFs) collected from adipose fat as a novel, independent microvascular unit for the development of new microvessels to provide blood flow to transplanted islets. MVFs exhibit high angiogenic activity and possess the unique ability to rapidly develop into microvascular networks in vitro. As described below, the release of microvessel fragments from human pancreas (pancreas-derived [PD]-MVFs) during human islet isolation has now been observed and a novel method to collect them has been established. These MVFs were derived from the exocrine tissue within the pancreas. Numerous PD-MVFs were released from the pancreatic tissue along with the intact islets during enzymatic digestion. However, during the subsequent processing of the pancreatic digest, these fragments were previously eliminated during subsequent washes utilizing centrifugation to pellet the islets and acinar tissue. The centrifugation forces (g force and time) were not sufficient to pellet the microvessel fragments and they remained in the supernatant that was discarded. Thus, the final islet product lacked MVFs.

Figure 2:
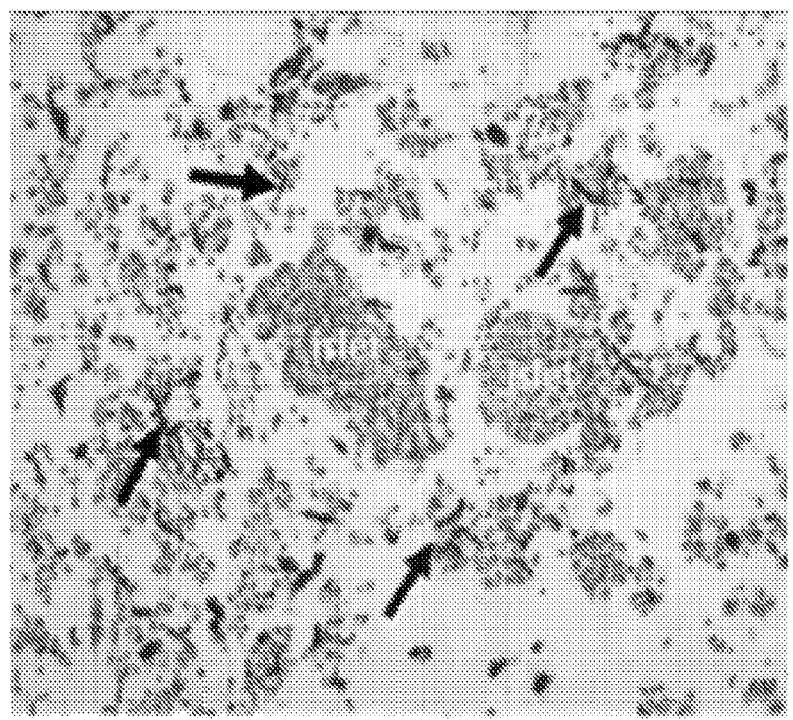
FIG. 2 is an image showing that numerous fragments are released during human islet isolation where histological analysis using CD31 staining (brown) demonstrates the presence of numerous PD-MVFs (arrows) with human islets.
Figure 3A:
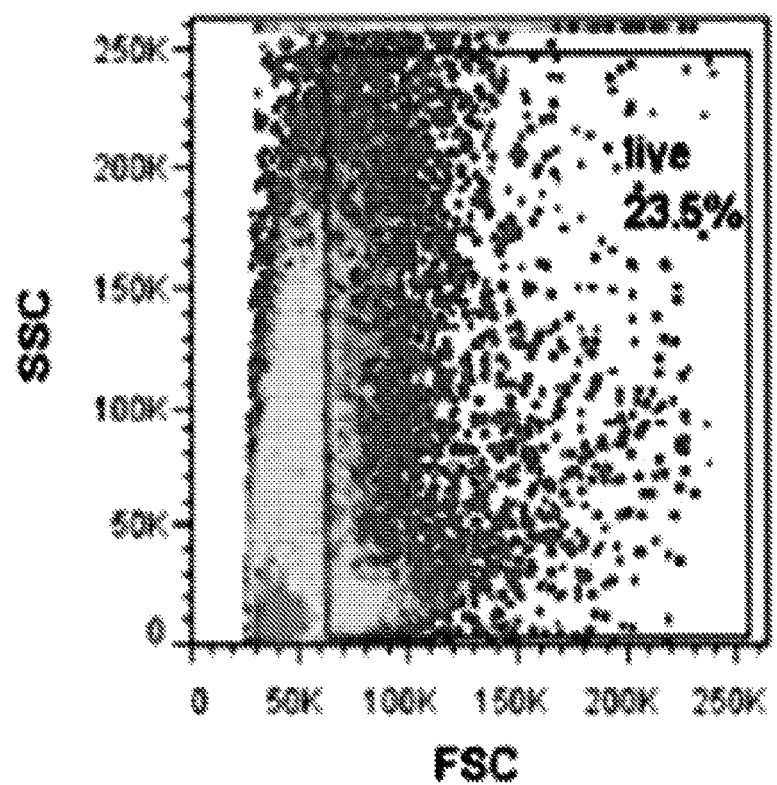
FIGS. 3A-3D includes graphs showing fluorescence activated cell sorting (FACS) analysis of PD-MVF samples collected after pancreas digestion that were filtered through a 100 μm mesh and stained for flow cytometric CD31 expression using LSRII cytometer, including graphs showing.
Figure 3B:
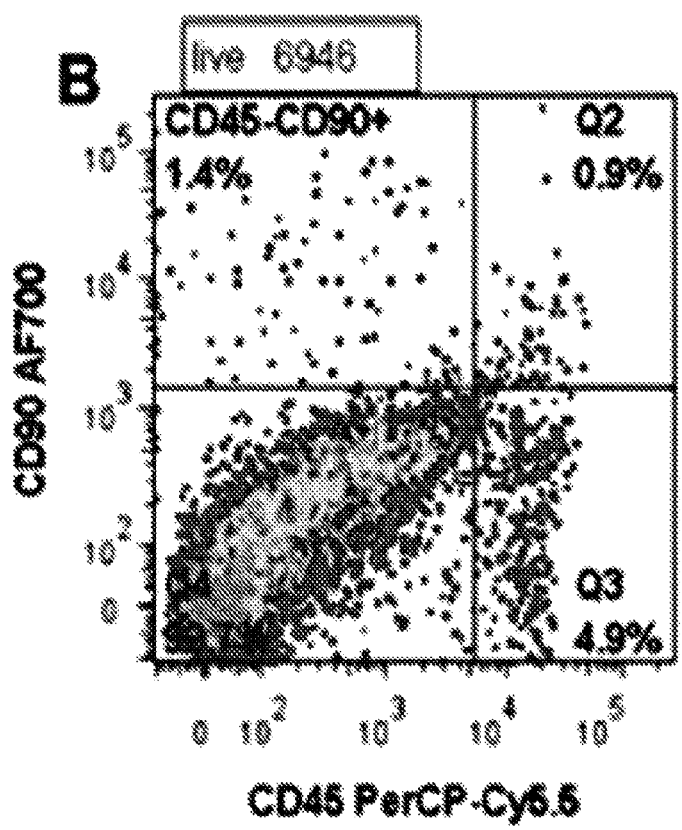
Figure 3C:
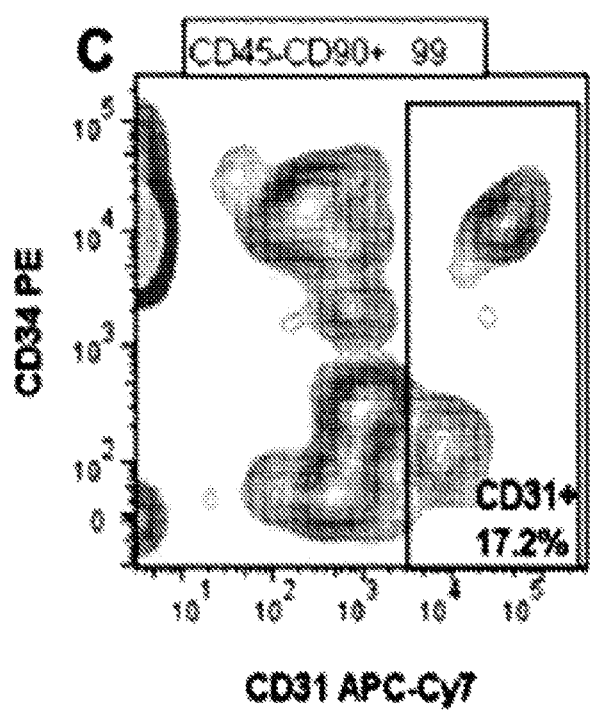
Figure 3D:
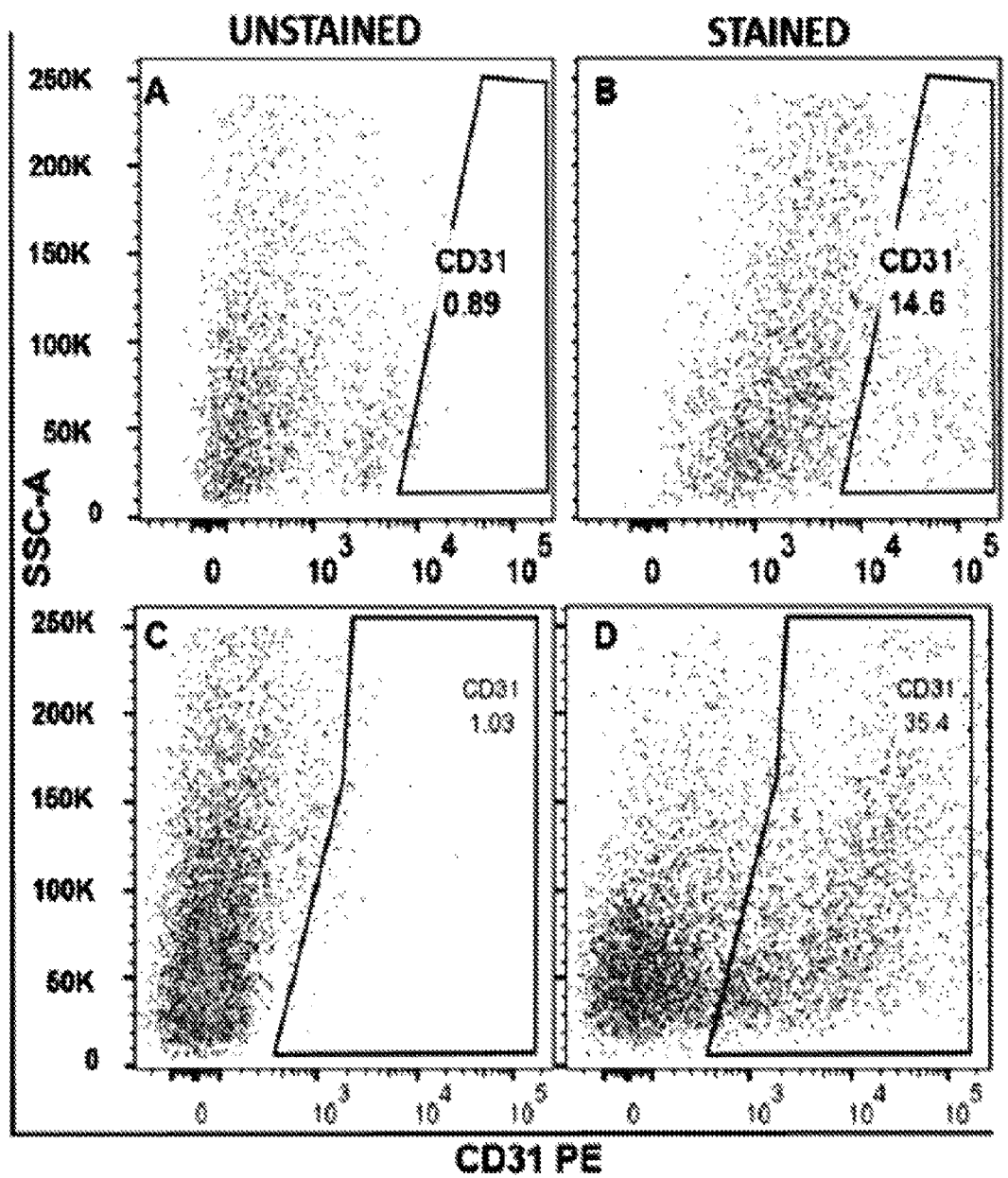
Figure 4A:
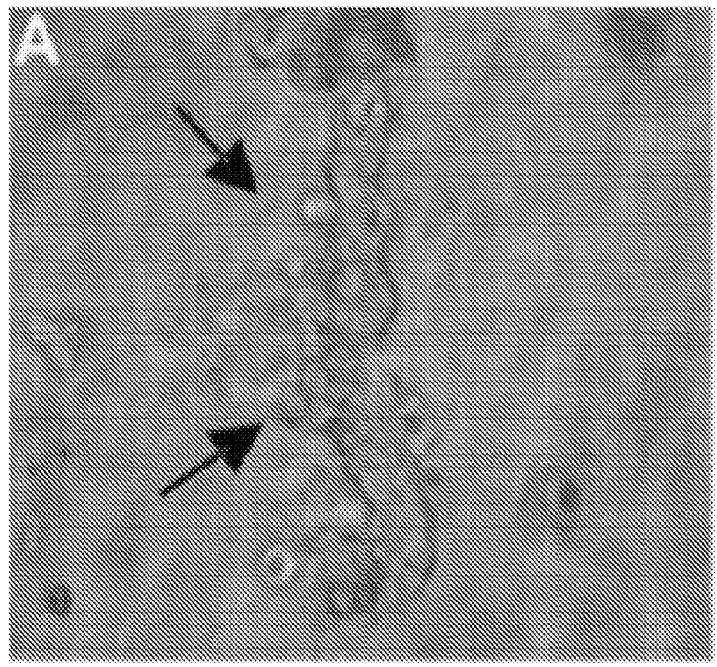
FIGS. 4A-4C include images showing the results of in vitro studies demonstrating that PD-MVFs undergo sprouting and network formation in PD-MVFs that were cultured in a collagen gel and monitored at different time-points for sprouting and network formation, including images showing.
Figure 4B:
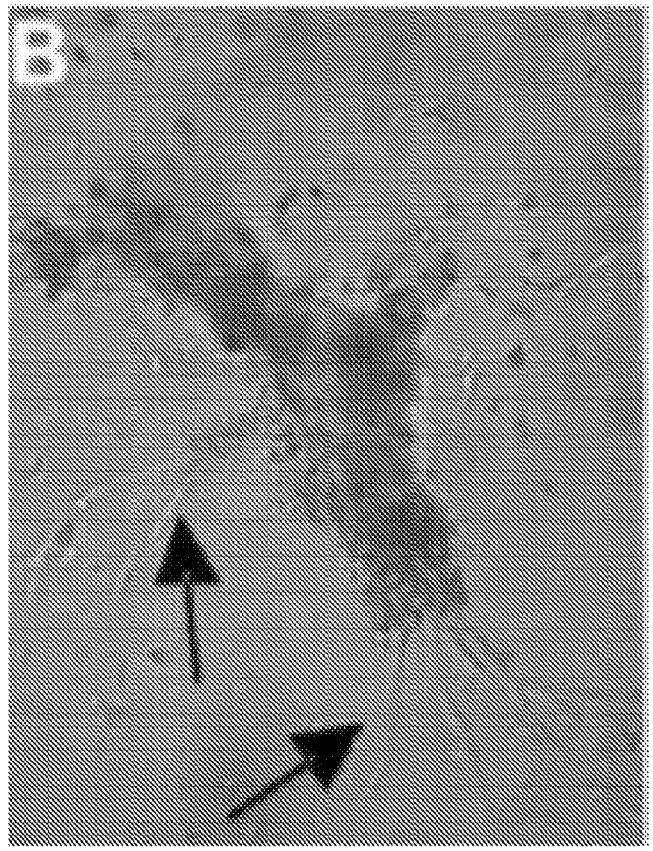
Figure 4C:
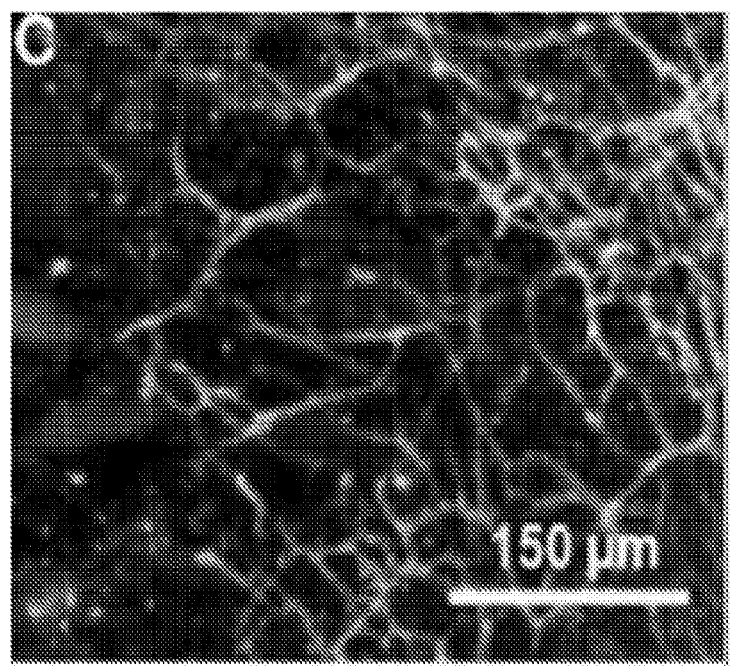

In that regard, to obtain the microvessel fragments of the presently-disclosed subject matter, a methodology was developed that subjected the initial centrifugation supernatant to a subsequent centrifugation at a higher g force to cause the microvessel fragments to pellet. These fragments could then be added back to the isolated islets to create an islet isolate enriched with microvessel fragments. In particular, for isolating AD-MVFs, the adipose tissue was first digested with collagenase for a short period and the fragments were then recovered based on size selection using nylon screens. A similar approach was used to separate pancreas-derived MVFs (PD-MVFs). During the human islet isolation procedure, the pancreatic tissue sample was first well perfused using standard enzyme combinations. The tissue was then digested using the Ricordi chamber in the presence of the same enzyme mix. After maximal tissue dissociation, the total volume of the digested tissue mixture was centrifuged. The supernatant obtained after centrifugation was passed though metallic sieves of specific pore sizes to capture PD-MVFs. An estimated 1 gm of rat pancreas digestion resulted in about 1-2 million cells whereas an estimated 0.45-0.55 million PD-MVF cells was obtained per gram of human pancreas. Morphological assessment of rodent and human PD-MVFs (FIGS. 1A-1F) using phase contrast microscopy revealed a vermiform appearance similar to AD-MVF. Higher magnification revealed a beaded structure with an endothelium lining, a morphology previously observed for AD-MVFs, while a scanning electron microscope (SEM) image demonstrated a magnified tubular structure of a PD-MVF. As shown in FIG. 2 (black arrows), the presence of endothelial cells (ECs) within MVFs was confirmed by CD31 staining. Furthermore, a FACS analysis (FIGS. 3A-3D) was performed to quantify endothelial cells (ECs) (CD31 antibody) within the PD-MVF samples. With the refined human PD-MVF preparations, a higher percentage (14-20%) of ECs was observed than previously seen. Rat PD-MVF samples, however, consistently showed a much higher percentage of ECs (25-35%, n=3). Other cellular sub-populations such as mesenchymal stem cells, immune cells and progenitor cells (CD90; CD73, CD117), ductal (CK19) cells were also identified in the samples. Overall, the sorting analysis revealed that PD-MVFs contained resident ECs, the building blocks for sprouting angiogenesis and network formation. It has been previously shown that MVFs are composed of cellular and extracellular components, which have been implicated during in vivo angiogenic processes. Further evaluation of the angiogenic potential of PD-MVFs was assessed by placing them ($1 \times 10^6$ cells/ml) in a collagen gel. Interestingly, sprouting was observed from within the PD-MVFs within 2 days after being cultured in 3D gel (FIG. 4A, arrows). The sprouting intensified at day 7 resulting in tubular structures resembling endothelial tip and stalk cell phenotypes (FIG. 4B, arrows). Network formation was observed at day 14 and the source of the tubular structures and vessel networks was confirmed to be endothelial in origin after staining with UEA-1 green (FIG. 4C). PD-MVFs and human islets were derived from the same tissue source.

Figure 5A:
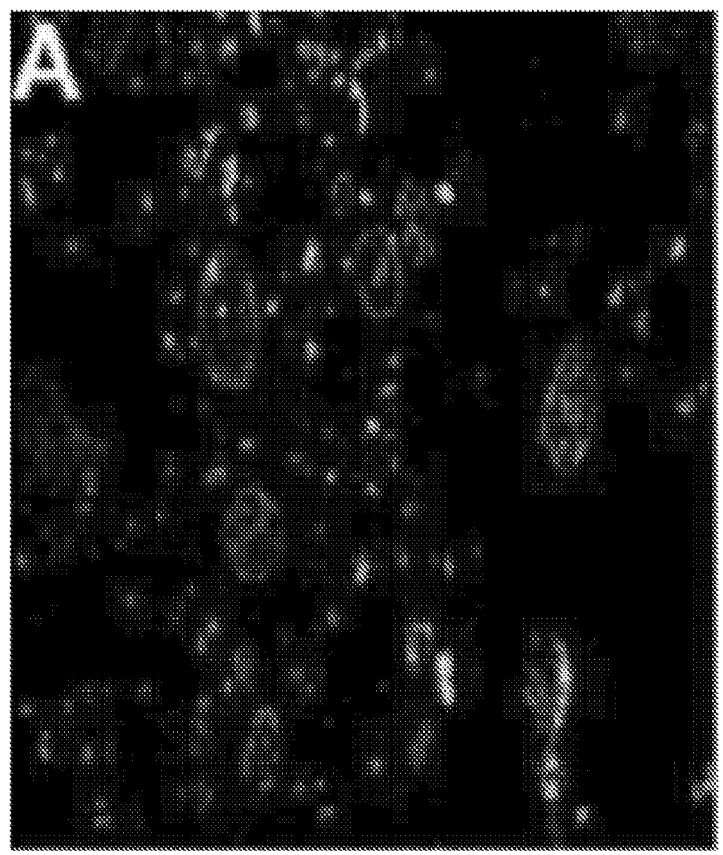
FIGS. 5A-5D include images showing PD-MVFs as potential islet neovascularization units where freshly isolated human islets and PD-MVFs were co-cultured in a collagen gel and evaluated at various time-points, where gels were taken out at specific time-points (day 0, 2, 7 and 14) and stained to show the presence of islets and vessel formation using insulin and UEA-1 stains respectively, and where the nuclei was stained using DAPI (blue color). Immunofluorescence staining of islets (insulin stain, red) and PD-MVFs (UEA-1, green) is shown at day 0 (FIG. 5A), day 2 (FIG. 5B), day 7 (FIG. 5C) and at day 14 (FIG. 5D). Standard staining protocols and confocal microscopy imaging were applied to all samples at the respective time-points.
Figure 5B:
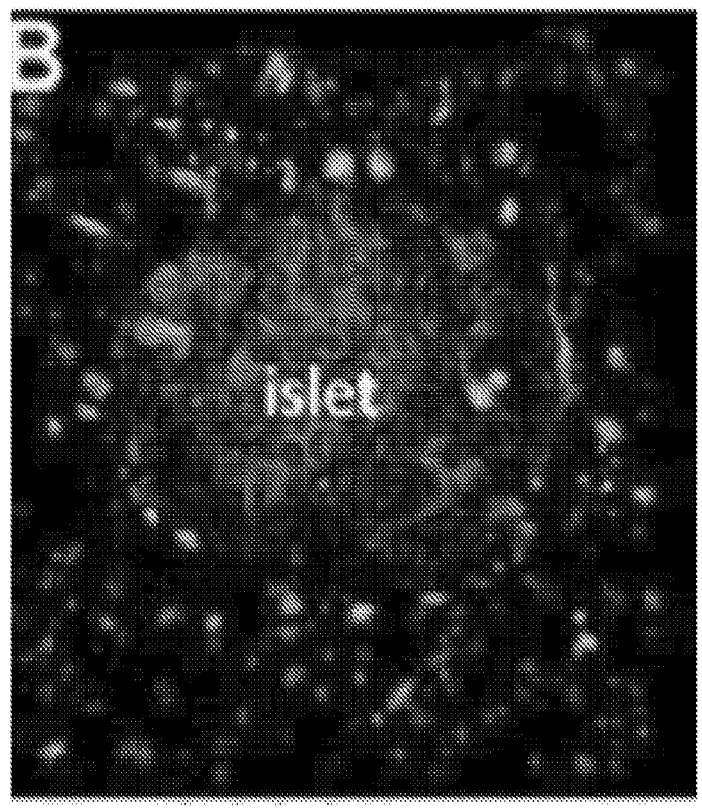
Figure 5C:
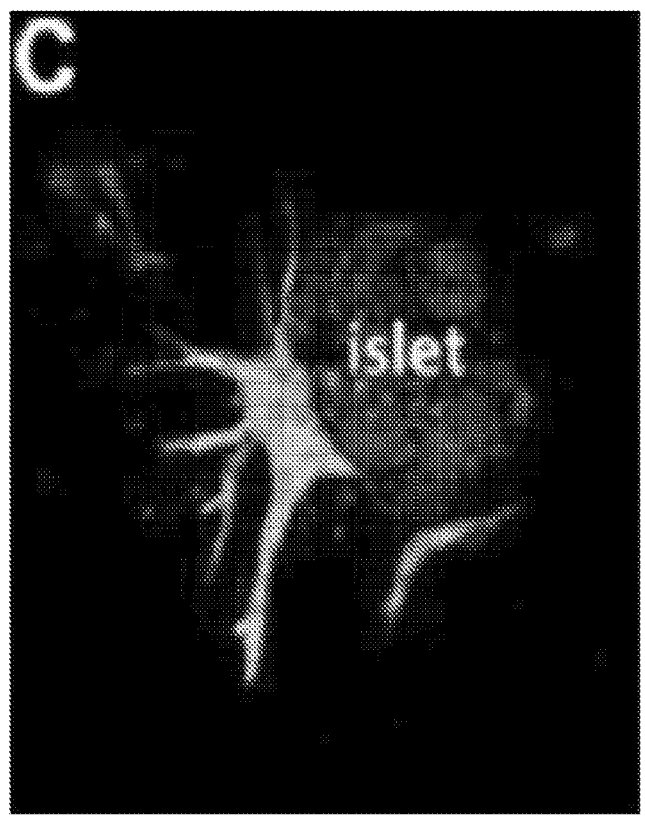
Figure 5D:
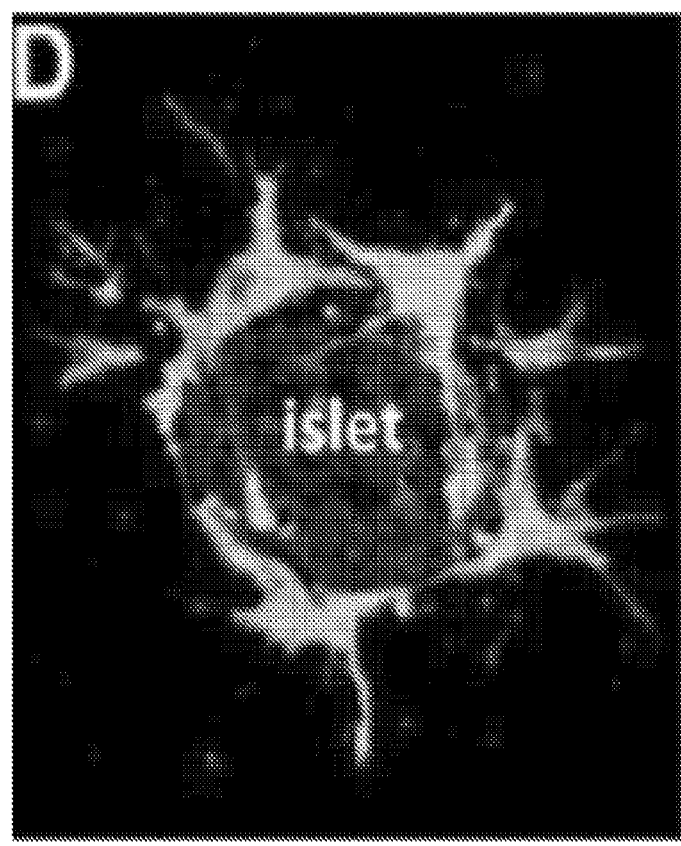
Figure 6A:
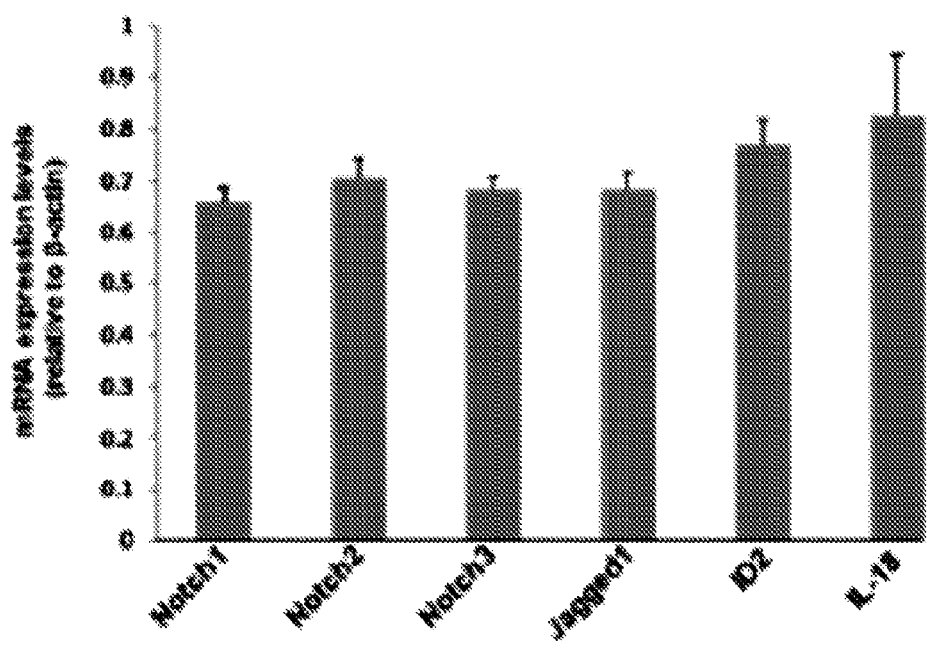
Figure 6B:
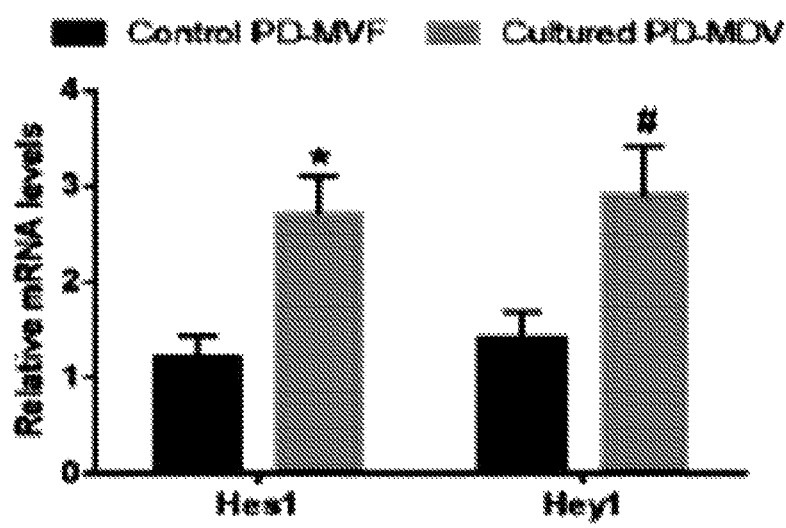

It was further hypothesized that PD-MVFs have the ability to support neovasculature formation in freshly isolated islets. Islets and PD-MVFs were co-cultured (1:1000 cells—respectively) in a 3D gel to determine the potential of PD-MVFs as novel islet neovascularization units. Immunofluorescence staining identified PD-MVFs (UEA-1, green) and islets (insulin, red) during in vitro co-culture studies (FIG. 5A). The progressive intensity of network formation was observed at day 2, day 7, and day 14 of the co-culture experiments (FIGS. 5B-5D). Gene expression studies (FIGS. 6A-6B) further revealed that Notch signaling pathway components played a role during PD-MVF network formation. Overall, these observations indicated that PD-MVFs have the capacity to form neovessels around islets and that these fragments have the capacity to be utilized as a vascular unit for co-transplantation with human islets.

Example 2—Investigation of Intra-Islet Sprouting.

Figure 7A:
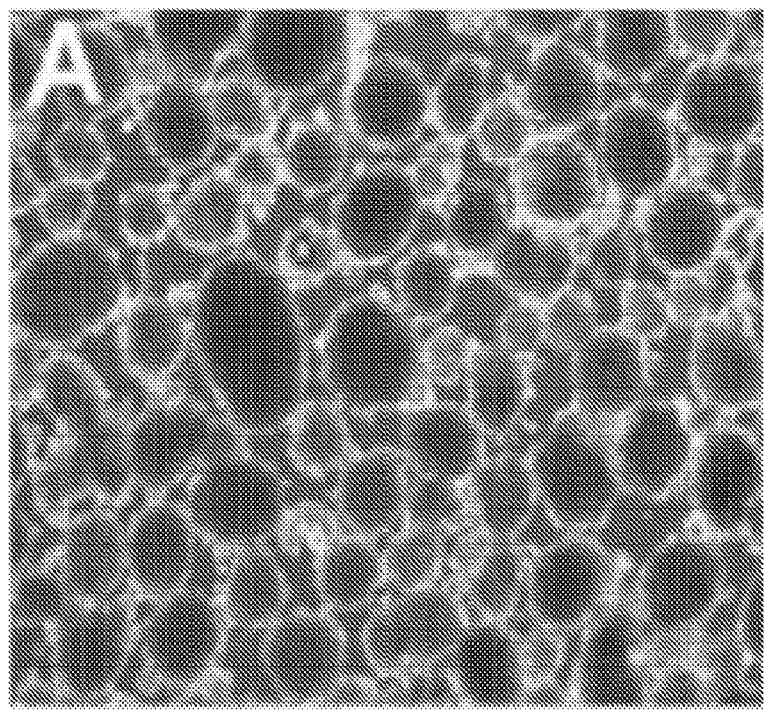
FIGS. 7A-7I include images showing that freshly isolated human islets when co-cultured with PD-MVFs (collagen gel) form peri-islet vessels (PIVs), including images showing: islets in standard culture media do not form PIVs as observed at (FIG. 7A) day 0 and at (FIG. 7B) day 14.
Figure 7B:
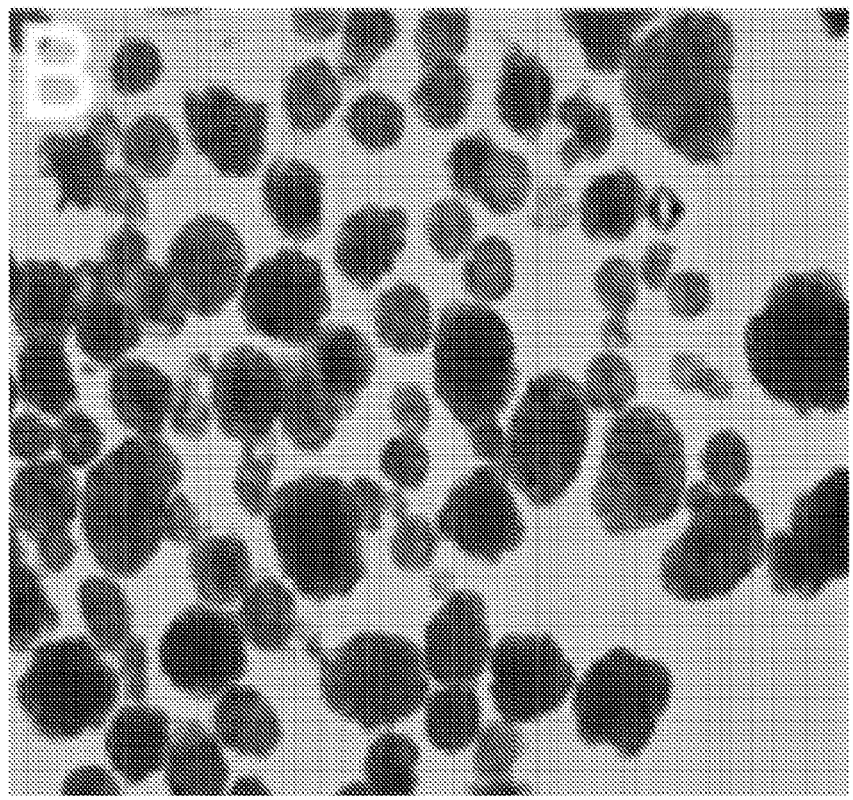
Figure 7C:
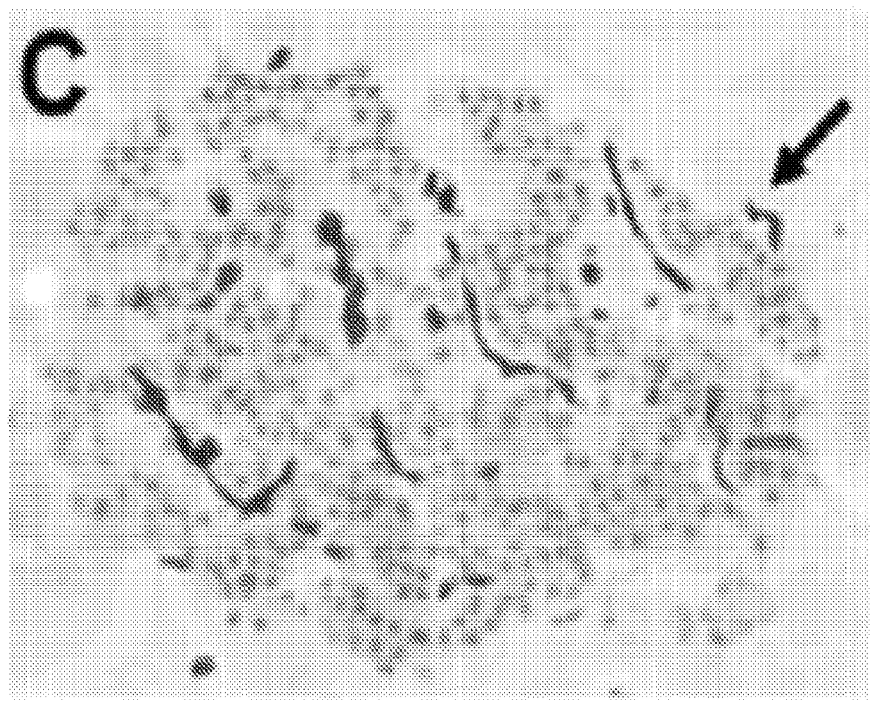
Figure 7D:
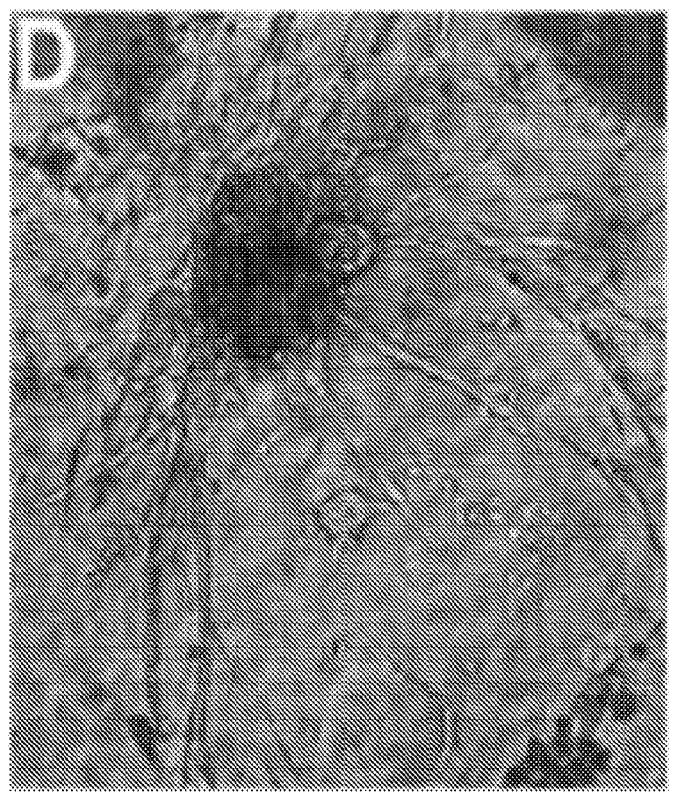
Figure 7E:
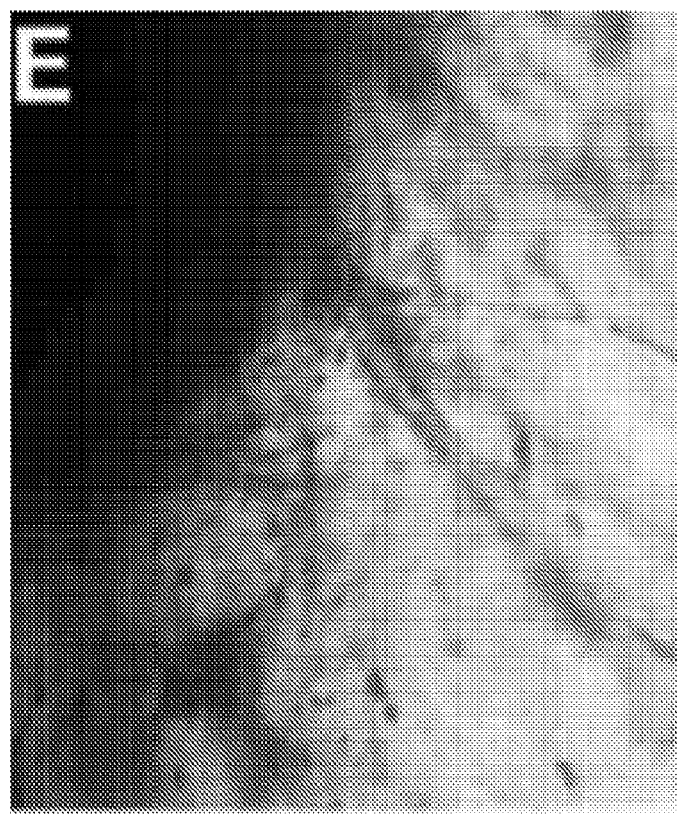
Figure 7F:
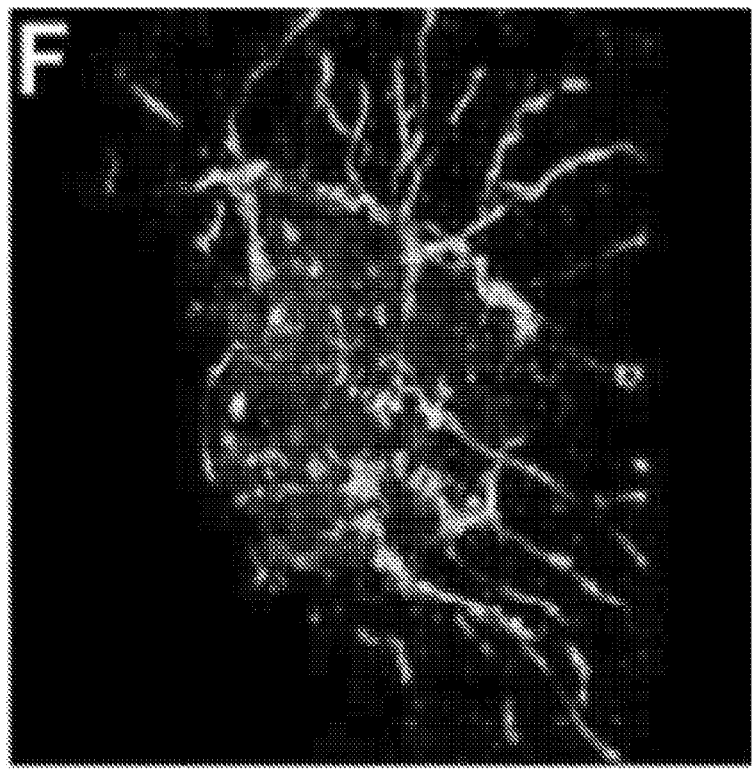
Figure 7G:
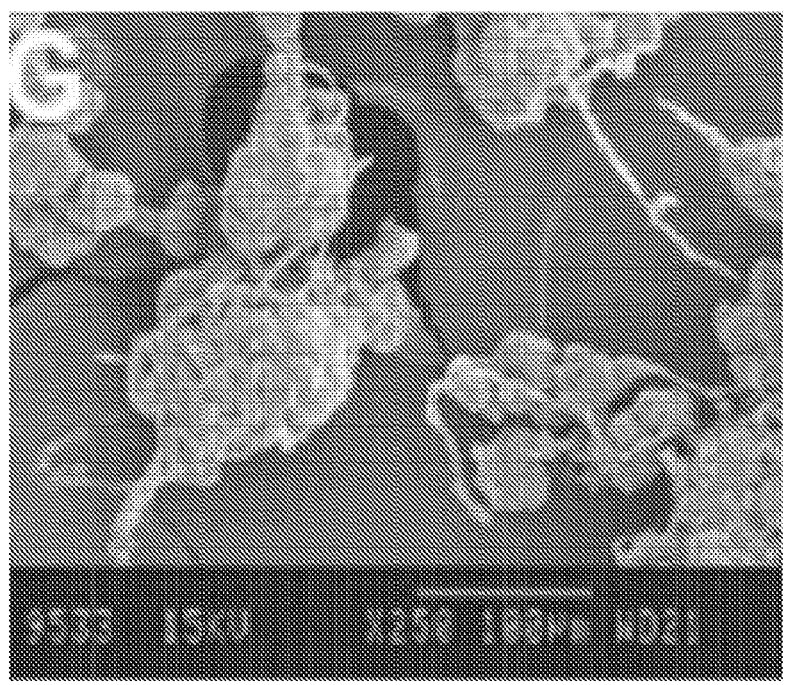
Figure 7H:
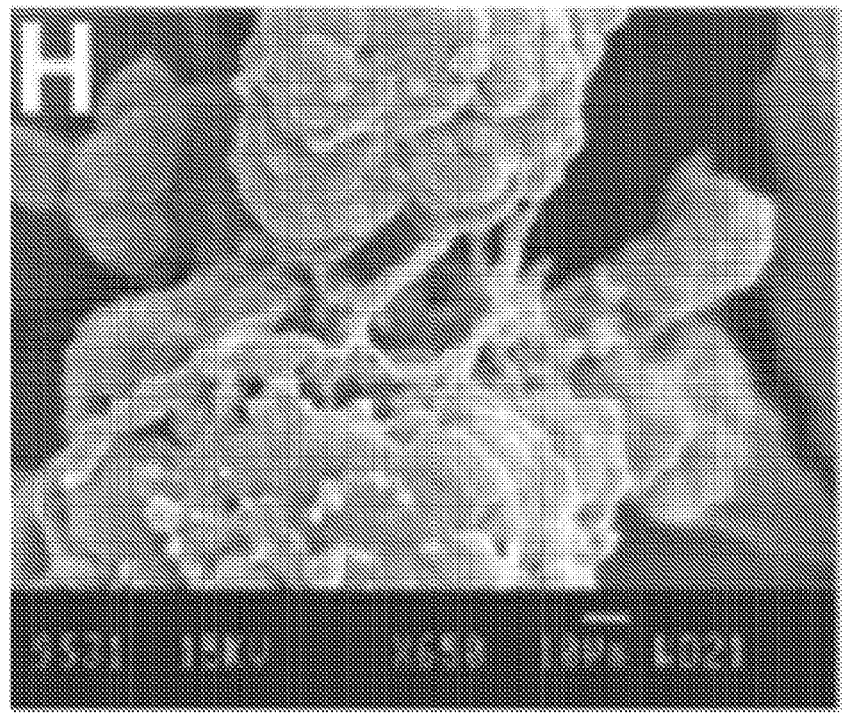
Figure 7I:
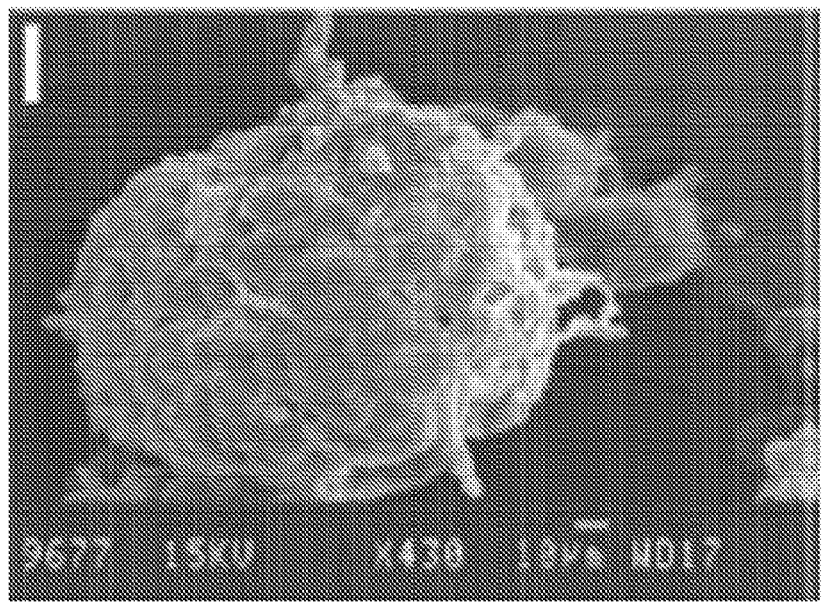
Figure 7J:
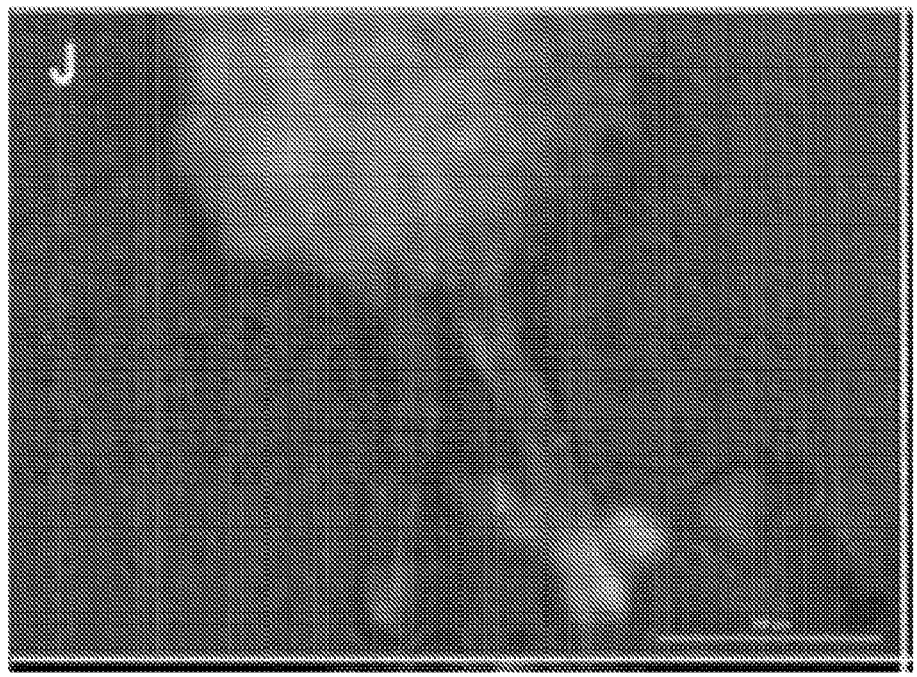
FIGS. 7J-7M include images showing that PD-MVFs stimulate intra-islet endothelial sprout formation, including images showing.
Figure 7K:
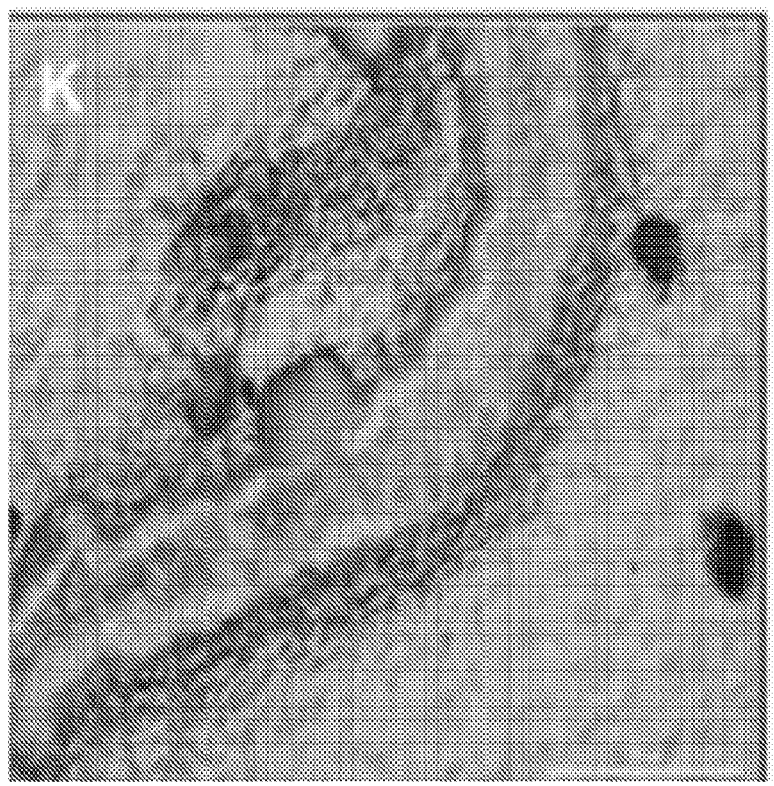
Figure 7L:
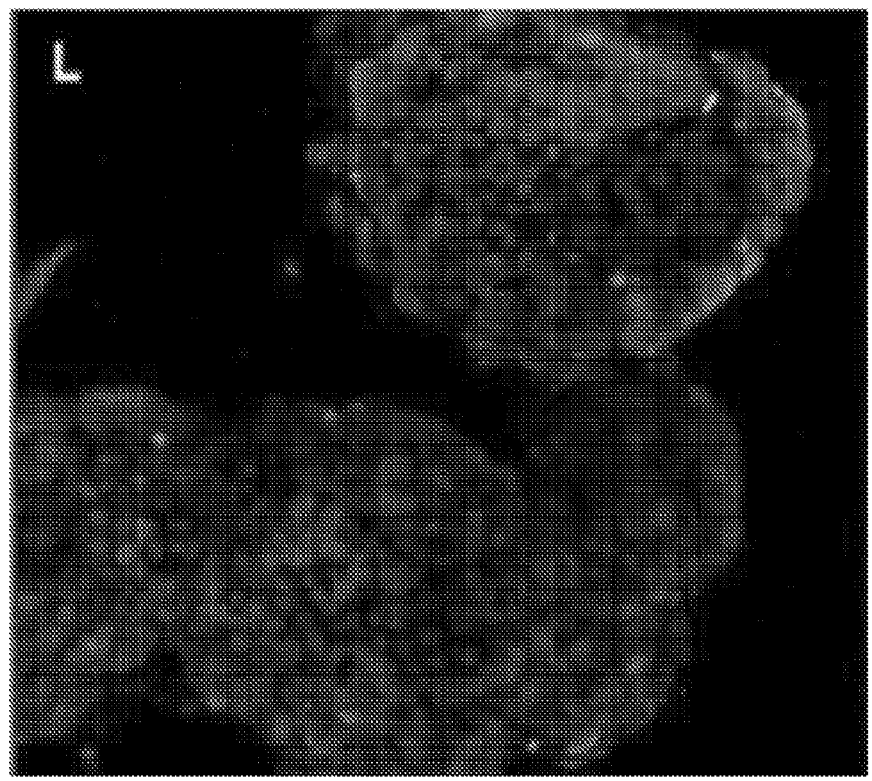
Figure 7M:
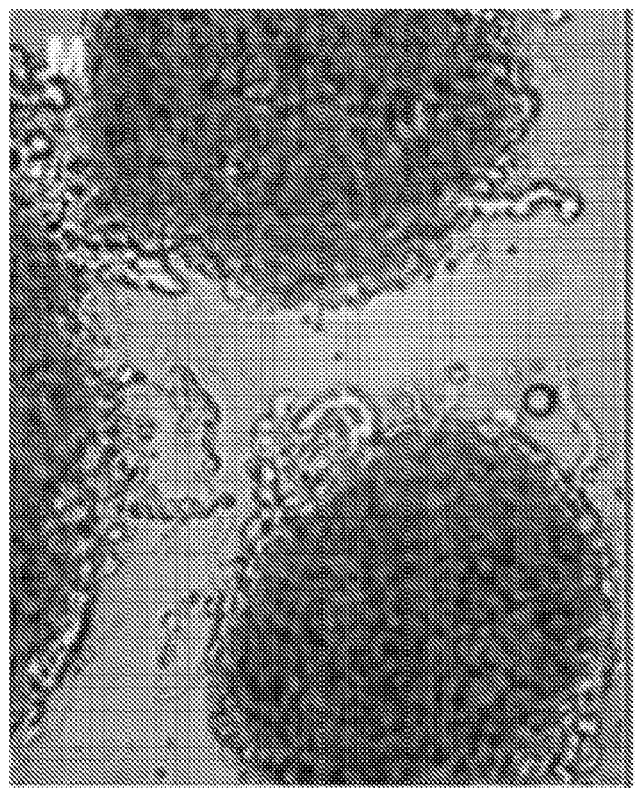
Figure 8:
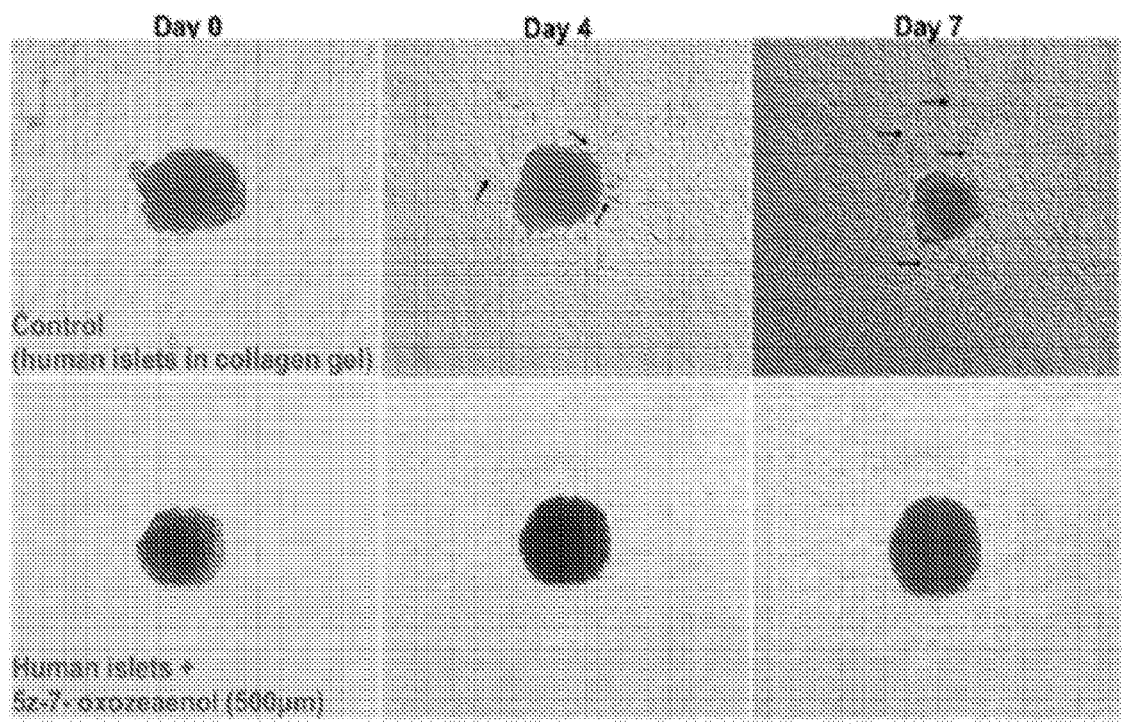
FIG. 8 includes images showing that inhibition of TAK1 prevents islet sprouting and PIV formation, including images showing sprout formation (arrow) from a human islet cultured in collagen gel (top panel), and showing inhibition of PIV and sprout formation from islets in the presence of TAK1 inhibitor (bottom panel).
Figure 9:
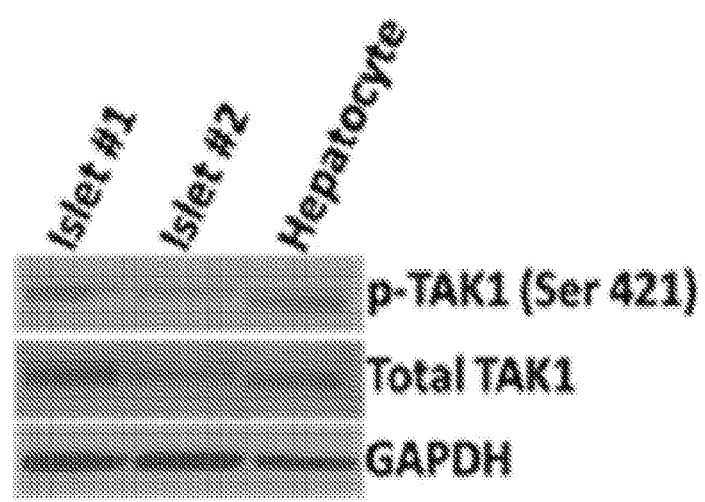
FIG. 9 includes images showing TAK1 is phosphorylated in freshly isolated islets, where a western blot analysis from two independent human islet protein lysates was performed to determine total (#5206, Cell Signaling) and phosphorylated levels (#9339, Cell Signaling) of TAK1, where GAPDH was used as a loading control, and where hepatocyte was used as positive control.

Freshly isolated human islets in the standard culture media do not have the ability to form cellular sprouts as observed at day 14 (FIG. 7B). However, co-culture and co-transplantation studies demonstrated that PD-MVFs stimulate intra-islet ECs to form peri-islet vessels (PIVs). Intra-islet endothelial structures were observed when islets were stained with CD31 (FIG. 7C, black arrow). Intense PIV formation was observed at day 14 of the co-culture (FIG. 7D). As observed for PD-MVFs, the source of these islet sprouts were endothelial in origin when islets were stained with UEA-1 (FIG. 7F). SEM images revealed the ultrastructure of PIVs from freshly isolated human islets (FIG. 7G-7I). The ability of freshly isolated human islets to form PIVs in presence of PD-MVFs indicated that PD-MVFs release pro-angiogenic paracrine factors which stimulate intra-islet ECs for survival and sprout formation. To test that hypothesis, rat GFP islets were co-cultured with regular non-GFP rat PD-MVFs (1:1000) in collagen gels and the phenotype was observed for 14 days. Stimulated intra-islet ECs formed PIVs (green hair-like projections from within GFP islets) and inosculated with the PD-MVF cells within the surrounding environment (FIGS. 7J-7K). That observation was further confirmed using Tie2 mice studies (GFP tagged ECs) which indicated that PD-MVFs released pro-angiogenic factors to stimulate intra-islet vessel growth (FIGS. 7L-7M). It was hypothesized that TAK1, a mitogen activating protein kinase played a role during islet EC survival. Human islets when cultured in a 3D collagen gel, in the presence of TAK1 inhibitor (5z-7-oxozeaenol) exhibited no sprouting at day 4 or day 7 (FIG. 8) when compared to the appropriate controls (black arrows, day 4 and day 7). TAK1 is an upstream MAP kinase involved in the activation of downstream kinases (MKK4, MKK3/6) which activate p38 MAPK and JNK respectively. Phosphorylation (Ser421) of TAK1 protein was observed in cell lysates of freshly isolated islets (FIG. 9) indicating that the molecule is activated to initiate pro-survival pathways in islets.

Example 3—Implantation of PD-MVF Constructs

Figure 10A:
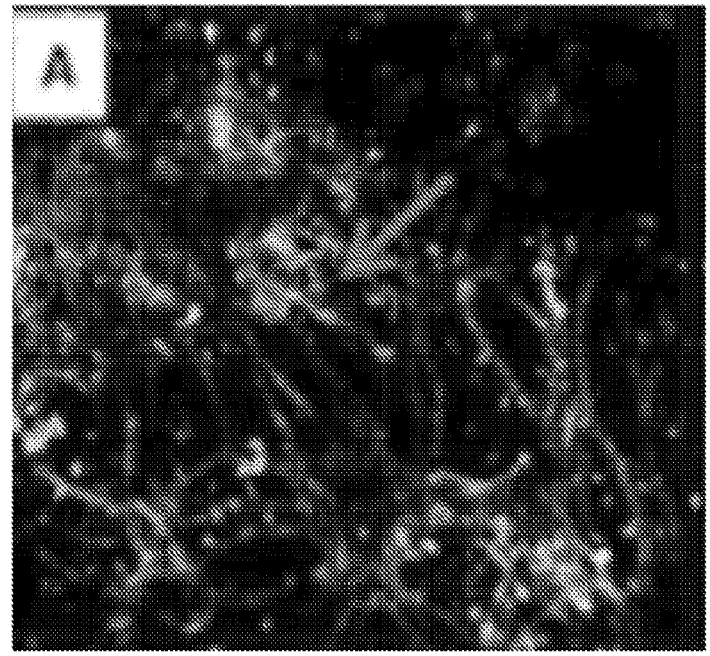
FIGS. 10A-10C include images showing that rodent islets and adipose-derived MVFs inosculate in vitro to form 'vascular baskets' after rodent islets and MVFs were co-cultured and stained using insulin (green) and GS-1 (endothelial stain, orange) at day 14, including images showing.
Figure 10B:
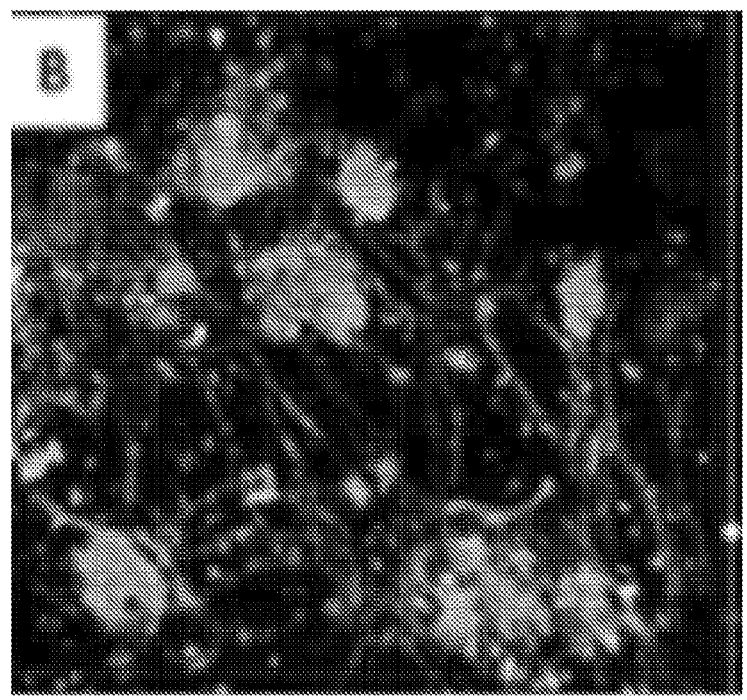
Figure 10C:
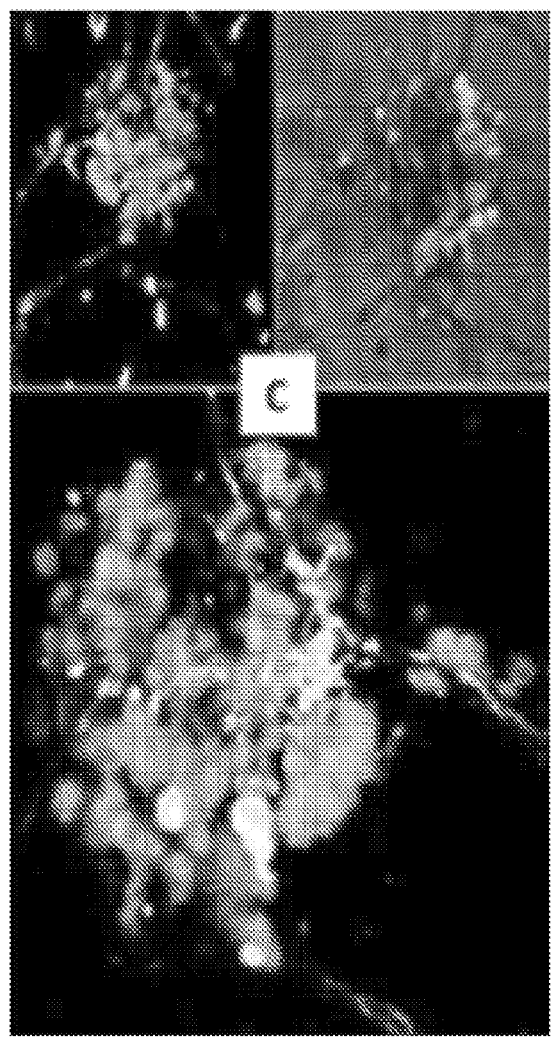
Figure 11A:
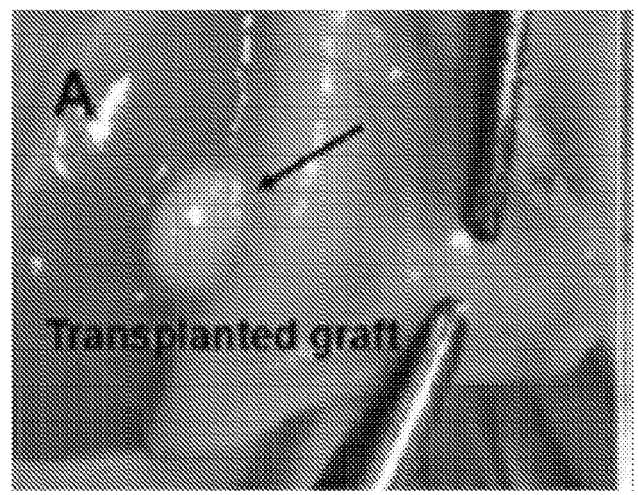
FIGS. 11A-11G includes images and a graphs showing that bioengineered islets (islets cultured in presence of MVFs) have potential to reverse diabetes, including.
Figure 11B:
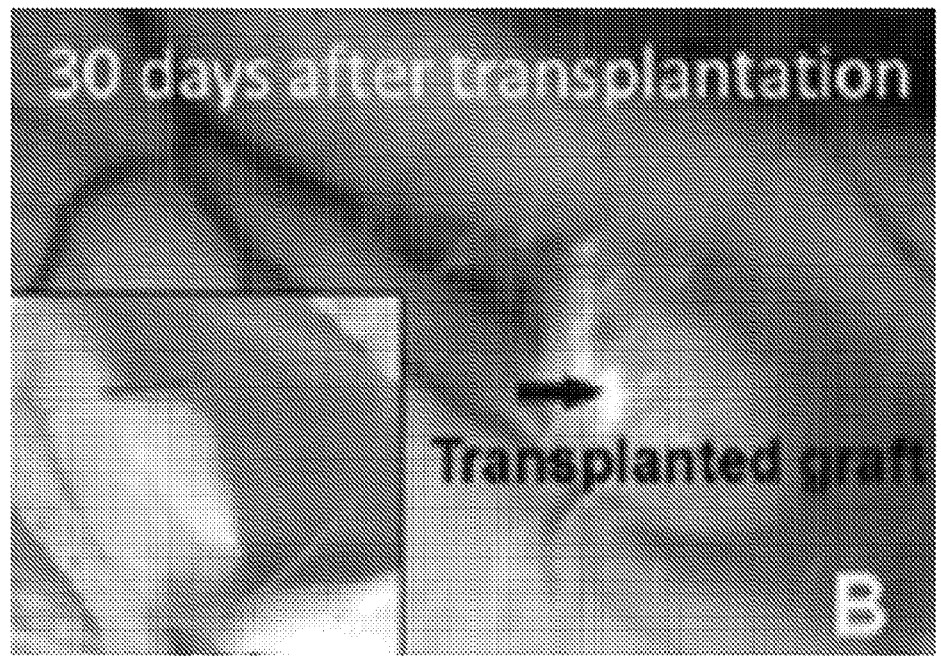
Figure 11C:
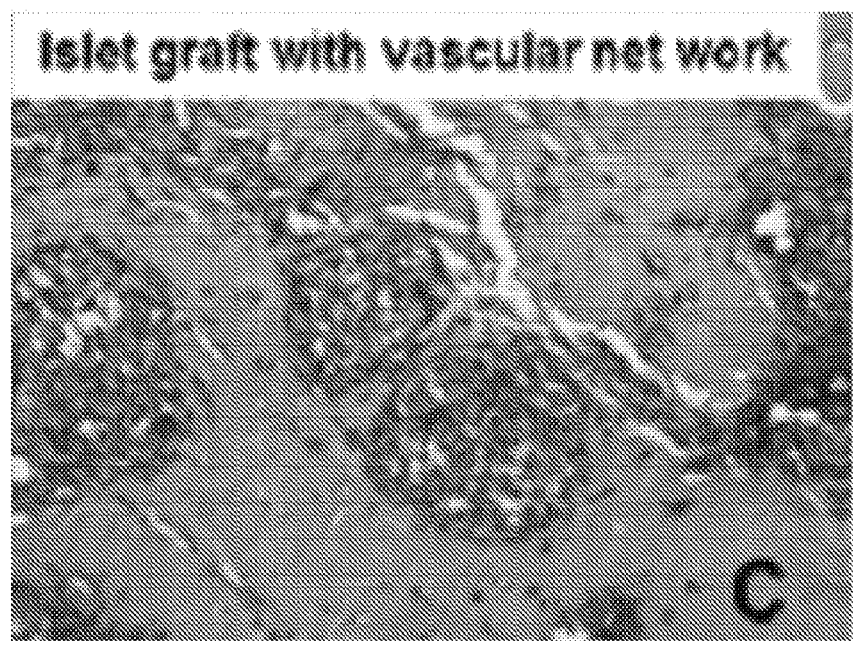
Figure 11D:
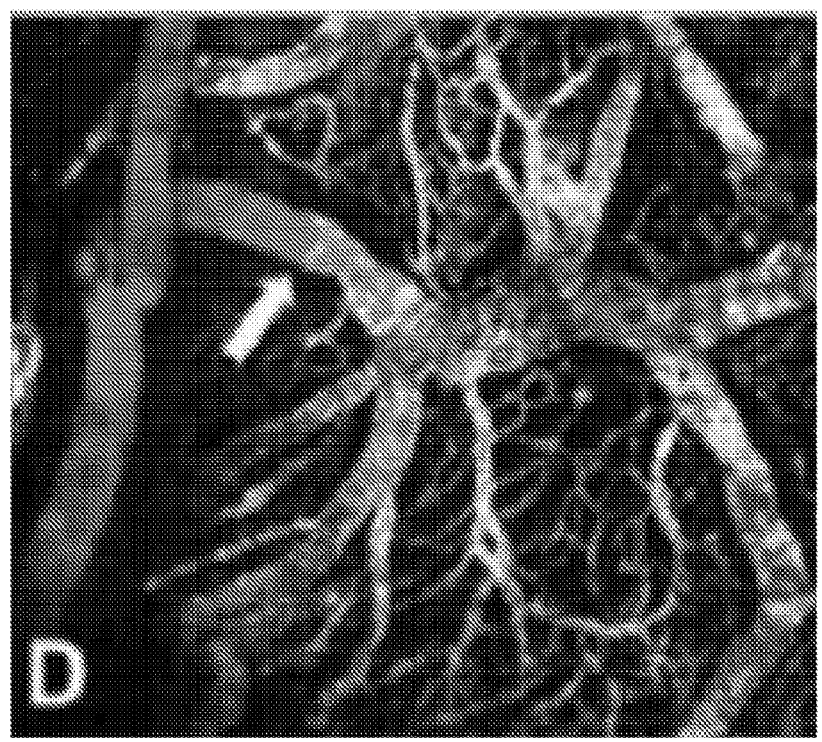
Figure 11E:
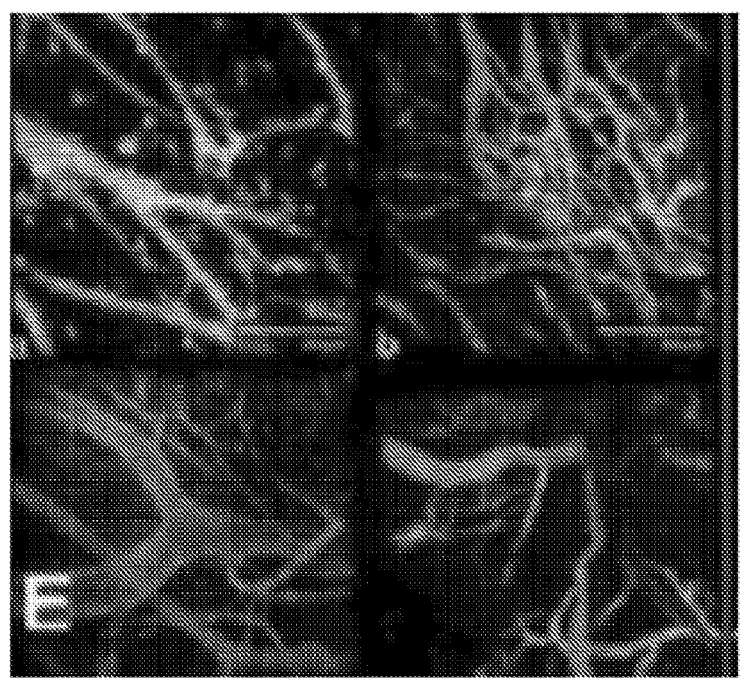
Figure 11F:
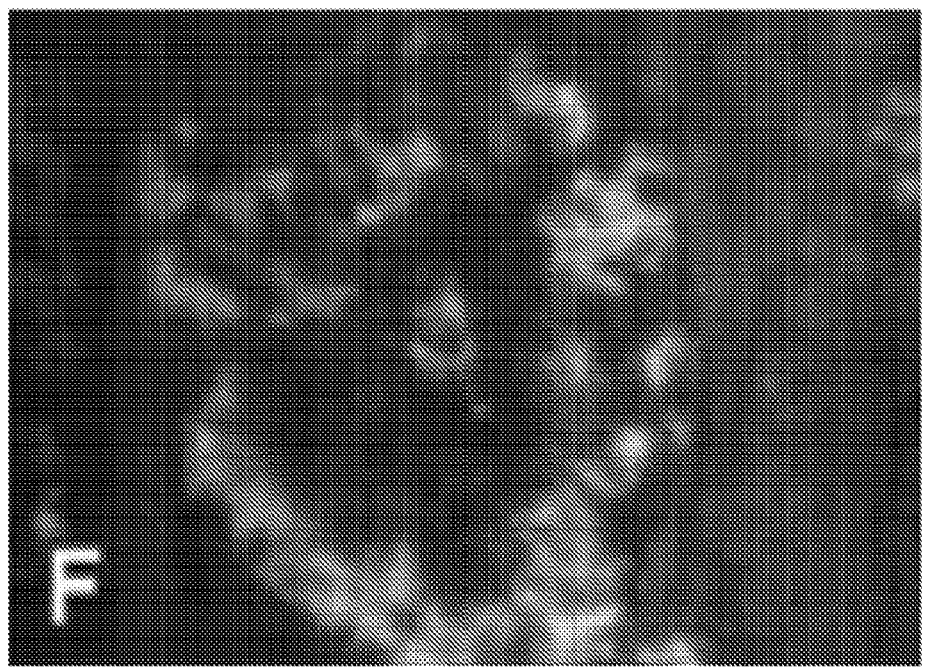
Figure 11G:
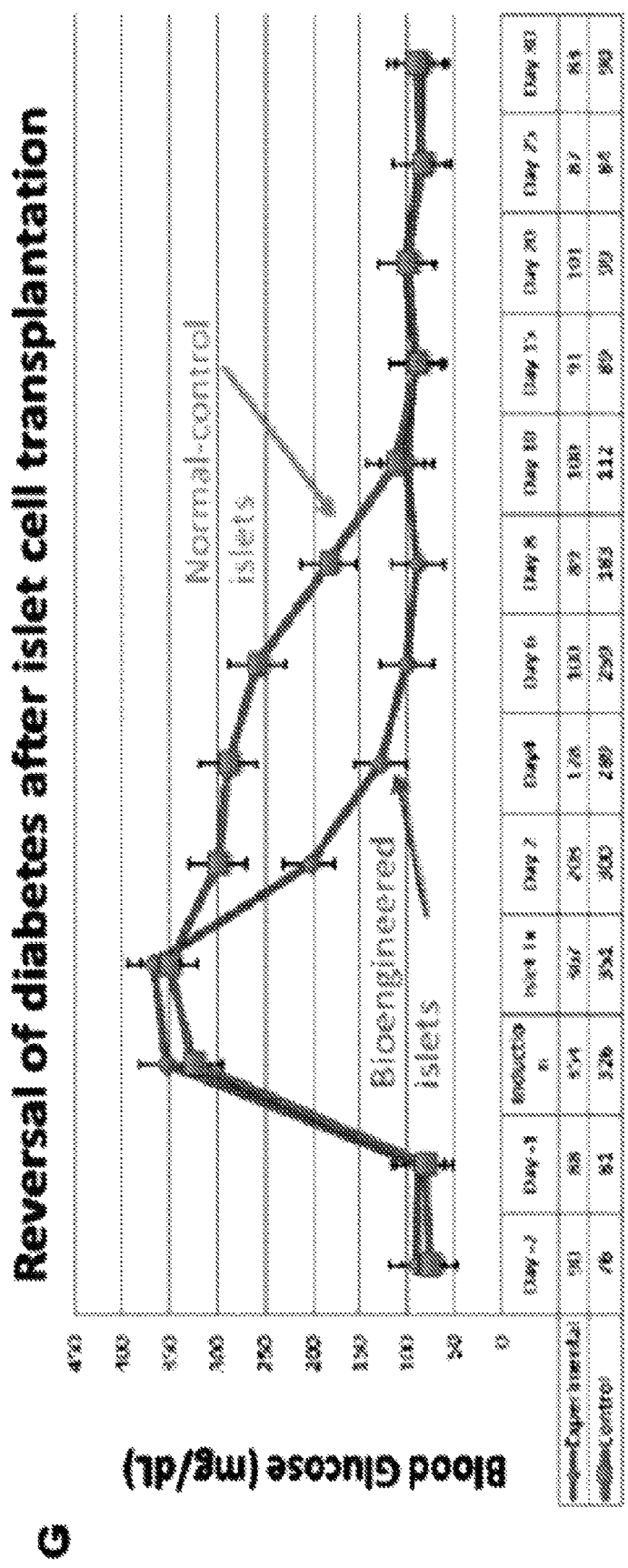

The ability to utilize PD-MVFs to support islet neovessel formation is clinically relevant. PD-MVFs can be used within prevascularized constructs and has immense potential to improve islet graft function. The in vitro studies demonstrated that rodent islets when co-cultured with adipose tissue-derived MVFs (1:1000) had the ability to form the structures which were termed as 'vascular baskets'. The MVFs formed intense networks around the islets, many of which inosculated with the intra-islet vasculature (FIGS. 10A-10C). In vivo studies demonstrated that constructs (PD-MVFs+islets) when transplanted into a nude mouse model were able to inosculate with the host vasculature within 7 days after implantation (FIG. 11B). Histology sections of the graft demonstrated the presence of islets embedded within the host tissue (FIG. 11C). Dextran infusion studies confirmed the inosculation of the host vessels with an adipose derived MVF graft (FIGS. 11D-11E), whereas the control islets had lesser vascular supply. Of importance, the islet-PD-MVF graft (bioengineered islets) demonstrated a quick reversal of diabetes (FIG. 11G) when compared to control islet graft.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. B. J. Hering, W. R. Clarke, N. D. Bridges, T. L. Eggerman, R. Alejandro, M. D. Bellin, K. Chaloner, C. W.

Czarniecki, J. S. Goldstein, L. G. Hunsicker, D. B. Kaufman, O. Korsgren, C. P. Larsen, X. Luo, J. F. Markmann, A. Naji, J. Oberholzer, A. M. Posselt, M. R. Rickels, C. Ricordi, M. A. Robien, P. A. Senior, A. M. Shapiro, P. G. Stock, N. A. Turgeon, C. Clinical Islet Transplantation, Phase 3 Trial of Transplantation of Human Islets in Type 1 Diabetes Complicated by Severe Hypoglycemia, Diabetes Care 39(7) (2016) 1230-40.
2. M. W. Laschke, M. D. Menger, Vascularization in tissue engineering: angiogenesis versus inosculation, Eur Surg Res 48(2) (2012) 85-92.
3. M. W. Laschke, Y. Harder, M. Amon, I. Martin, J. Farhadi, A. Ring, N. Torio-Padron, R. Schramm, M. Rucker, D. Junker, J. M. Haufel, C. Carvalho, M. Heberer, G. Germann, B. Vollmar, M. D. Menger, Angiogenesis in tissue engineering: breathing life into constructed tissue substitutes, Tissue Eng 12(8) (2006) 2093-104.
4. M. Brissova, K. Aamodt, P. Brahmachary, N. Prasad, J. Y. Hong, C. Dai, M. Mellati, A. Shostak, G. Poffenberger, R. Aramandla, S. E. Levy, A. C. Powers, Islet microenvironment, modulated by vascular endothelial growth factor-A signaling, promotes beta cell regeneration, Cell Metab 19(3) (2014) 498-511.
5. S. Rafii, J. M. Butler, B. S. Ding, Angiocrine functions of organ-specific endothelial cells, Nature 529(7586) (2016) 316-25.
6. J. Rehman, D. Traktuev, J. Li, S. Merfeld-Clauss, C. J. Temm-Grove, J. E. Bovenkerk, C. L. Pell, B. H. Johnstone, R. V. Considine, K. L. March, Secretion of angiogenic and antiapoptotic factors by human adipose stromal cells, Circulation 109(10) (2004) 1292-8.
7. S. Narayanan, G. Loganathan, M. Dhanasekaran, W. Tucker, A. Patel, V. Subhashree, S. Mokshagundam, M. G. Hughes, S. K. Williams, A. N. Balamurugan, Intra-islet endothelial cell and beta-cell crosstalk: Implication for islet cell transplantation, World J Transplant 7(2) (2017) 117-128.
8. D. Talavera-Adame, A. Gupta, S. Kurtovic, K. L. Chaiboonma, V. Arumugaswami, D. C. Dafoe, Bone morphogenetic protein-2/-4 upregulation promoted by endothelial cells in coculture enhances mouse embryoid body differentiation, Stem Cells Dev 22(24) (2013) 3252-60.
9. J. Olerud, D. Mokhtari, M. Johansson, G. Christoffersson, J. Lawler, N. Welsh, P. O. Carlsson, Thrombospondin-1: an islet endothelial cell signal of importance for beta-cell function, Diabetes 60(7) (2011) 1946-54.
10. G. Nikolova, N. Jabs, I. Konstantinova, A. Domogatskaya, K. Tryggvason, L. Sorokin, R. Fassler, G. Gu, H. P. Gerber, N. Ferrara, D. A. Melton, E. Lammert, The vascular basement membrane: a niche for insulin gene expression and Beta cell proliferation, Dev Cell 10(3) (2006) 397-405.
11. X. Pan, W. Xue, Y. Li, X. Feng, X. Tian, C. Ding, Islet graft survival and function: concomitant culture and transplantation with vascular endothelial cells in diabetic rats, Transplantation 92(11) (2011) 1208-14.
12. M. J. Bernas, F. L. Cardoso, S. K. Daley, M. E. Weinand, A. R. Campos, A. J. Ferreira, J. B. Hoying, M. H. Witte, D. Brites, Y. Persidsky, S. H. Ramirez, M. A. Brito, Establishment of primary cultures of human brain microvascular endothelial cells to provide an in vitro cellular model of the blood-brain barrier, Nat Protoc 5(7) (2010) 1265-72.
13. B. R. Shepherd, J. B. Hoying, S. K. Williams, Microvascular transplantation after acute myocardial infarction, Tissue Eng 13(12) (2007) 2871-9.
14. M. W. Laschke, S. Kleer, C. Scheuer, S. Schuler, P. Garcia, D. Eglin, M. Alini, M. D. Menger, Vascularisation of porous scaffolds is improved by incorporation of adipose tissue-derived microvascular fragments, Eur Cell Mater 24 (2012) 266-77.
15. B. R. Shepherd, H. Y. Chen, C. M. Smith, G. Gruionu, S. K. Williams, J. B. Hoying, Rapid perfusion and network remodeling in a microvascular construct after implantation, Arterioscler Thromb Vasc Biol 24(5) (2004) 898-904.
16. S. Sigrist, A. Mechine-Neuville, K. Mandes, V. Calenda, S. Braun, G. Legeay, J. P. Bellocq, M. Pinget, L. Kessler, Influence of VEGF on the viability of encapsulated pancreatic rat islets after transplantation in diabetic mice, Cell Transplant 12(6) (2003) 627-35.
17. D. Nyqvist, S. Speier, R. Rodriguez-Diaz, R. D. Molano, S. Lipovsek, M. Rupnik, A. Dicker, E. Ilegems, E. Zahr-Akrawi, J. Molina, M. Lopez-Cabeza, S. Villate, M. H. Abdulreda, C. Ricordi, A. Caicedo, A. Pileggi, P. O. Berggren, Donor islet endothelial cells in pancreatic islet revascularization, Diabetes 60(10) (2011) 2571-7.
18. T. Linn, K. Schneider, H. P. Hammes, K. T. Preissner, H. Brandhorst, E. Morgenstern, F. Kiefer, R. G. Bretzel, Angiogenic capacity of endothelial cells in islets of Langerhans, FASEB J 17(8) (2003) 881-3.
19. G. Loganathan, V. Subhashree, A. G. Breite, W. W. Tucker, S. Narayanan, M. Dhanasekaran, S. Mokshagundam, M. L. Green, M. G. Hughes, S. K. Williams, F. E. Dwulet, R. C. McCarthy, A. N. Balamurugan, Beneficial effect of recombinant rC1rC2 collagenases on human islet function: Efficacy of low-dose enzymes on pancreas digestion and yield, Am J Transplant 18(2) (2018) 478-485.
20. A. N. Balamurugan, B. Naziruddin, A. Lockridge, M. Tiwari, G. Loganathan, M. Takita, S. Matsumoto, K. Papas, M. Trieger, H. Rainis, T. Kin, T. W. Kay, S. Wease, S. Messinger, C. Ricordi, R. Alejandro, J. Markmann, J. Kerr-Conti, M. R. Rickels, C. Liu, X. Zhang, P. Witkowski, A. Posselt, P. Maffi, A. Secchi, T. Berney, P. J. O'Connell, B. J. Hering, F. B. Barton, Islet product characteristics and factors related to successful human islet transplantation from the Collaborative Islet Transplant Registry (CITR) 1999-2010, Am J Transplant 14(11) (2014) 2595-606.
21. K. K. Papas, C. K. Colton, R. A. Nelson, P. R. Rozak, E. S. Avgoustiniatos, W. E. Scott, 3rd, G. M. Wildey, A. Pisania, G. C. Weir, B. J. Hering, Human islet oxygen consumption rate and DNA measurements predict diabetes reversal in nude mice, Am J Transplant 7(3) (2007) 707-13.
22. A. N. Balamurugan, J. He, F. Guo, D. B. Stolz, S. Bertera, X. Geng, X. Ge, M. Trucco, R. Bottino, Harmful delayed effects of exogenous isolation enzymes on isolated human islets: relevance to clinical transplantation, Am J Transplant 5(11) (2005) 2671-81.
23. Hiscox A M, Stone A L, Limesand S, Hoying J B, Williams S K. An Islet-Stabilizing Implant Constructed Using a Preformed Vasculature. Tissue Eng. 2007. Epub 2007, Dec. 25. doi: 10.1089/ten.2007.0099. PubMed PMID: 18154456.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A tissue construct, comprising (i) a microvessel fragment derived from exocrine tissue of a pancreas and (ii) a pancreatic islet cell.

2. The tissue construct of claim 1, further comprising a biocompatible medium.

3. The tissue construct of claim 2, wherein the biocompatible medium comprises a hydrogel.

4. The tissue construct of claim 3, wherein the hydrogel is comprised of a material selected from the group consisting of agarose, alginate, collagen, fibrinogen, fibrin, laminin, a polyoxyethylene-polyoxypropylene block copolymer, silicone, polysaccharide, polyethylene glycol, and polyurethane.

5. The tissue construct of claim 4, wherein the hydrogel is comprised of collagen type I.

6. The tissue construct of claim 1, wherein the microvessel fragment derived from exocrine tissue of a pancreas and the pancreatic islet cell are obtained from a human.

7. The tissue construct of claim 1, wherein the tissue construct further comprises one or more Relevant Cells or one or more stem cells.

8. A tissue construct, comprising:
    a microvessel fragment derived from exocrine tissue of a pancreas; and
    one or more Relevant Cells and/or one or more stem cells.

9. The tissue construct of claim 8, further comprising a biocompatible medium.

10. The tissue construct of claim 9, wherein the biocompatible medium comprises a hydrogel.

11. The tissue construct of claim 10, wherein the hydrogel is comprised of a material selected from the group consisting of agarose, alginate, collagen, fibrinogen, fibrin, laminin, a polyoxyethylene-polyoxypropylene block copolymer, silicone, polysaccharide, polyethylene glycol, and polyurethane.

12. The tissue construct of claim 11, wherein the hydrogel is comprised of collagen type I.

13. A method for enriching microvessel fragments derived from exocrine tissue of a pancreas, comprising:
    subjecting an amount of pancreatic tissue to an enzymatic digestion to produce a slurry of digested pancreatic tissue;
    centrifuging the slurry of digested tissue in a first centrifuge tube at about 100 G to 200 G to deposit endocrine and exocrine tissue at the bottom of the centrifuge tube;
    collecting the supernatant from the first centrifuge tube in a second centrifuge tube; and
    centrifuging the supernatant at about 2000 G to pellet an amount of microvessel fragments derived from exocrine tissue of a pancreas.

14. The method of claim 13, further comprising a step of isolating an amount of pancreatic islet cells from the pancreatic tissue.

15. A method for treating diabetes, comprising administering to a subject in need thereof an effective amount of the tissue construct of claim 1 comprising microvessel fragment derived from exocrine tissue of a pancreas and a pancreatic islet cell.

16. The method of claim 15, wherein administering the tissue construct comprises subcutaneously administering the tissue construct.

17. The method of claim 16, wherein subcutaneously administering the tissue construct comprises subcutaneously administering the tissue construct at multiple sites in a body of a subject.

18. The method of claim 15, wherein the microvessel fragment derived from exocrine tissue of a pancreas and the pancreatic islet cell are incorporated into a biocompatible medium.

19. The method of claim 15, wherein the microvessel fragment derived from exocrine tissue of a pancreas and the pancreatic islet cell are obtained from the subject.

* * * * *